(12) United States Patent
Morgan et al.

(10) Patent No.: US 8,323,293 B2
(45) Date of Patent: Dec. 4, 2012

(54) TACK OR DRIVE SCREW FOR SECURING A PROSTHESIS TO BONE AND ASSOCIATED INSTRUMENTATION AND METHOD

(75) Inventors: Mickey Morgan, Frisco, TX (US); John Peloza, Dallas, TX (US); Randall Lee, Arlington, TX (US); Michael Keane, Downingtown, PA (US); William Miller, Downingtown, PA (US); James Talbot, Lititz, PA (US); Daniel Vennard, Clayton, DE (US); Josef Gabelberger, West Chester, PA (US)

(73) Assignee: Synthes GmbH, Oberdorf (CH)

( * ) Notice: Subject to any disclaimer, the term of this patent is extended or adjusted under 35 U.S.C. 154(b) by 160 days.

(21) Appl. No.: 12/810,986

(22) PCT Filed: Dec. 29, 2008

(86) PCT No.: PCT/US2008/088462
§ 371 (c)(1),
(2), (4) Date: Jun. 28, 2010

(87) PCT Pub. No.: WO2009/086523
PCT Pub. Date: Jul. 9, 2009

(65) Prior Publication Data
US 2010/0286703 A1    Nov. 11, 2010

Related U.S. Application Data

(60) Provisional application No. 61/017,402, filed on Dec. 28, 2007.

(51) Int. Cl.
*A61B 17/56* (2006.01)

(52) U.S. Cl. .......... 606/99; 606/104; 606/279; 606/329; 227/119; 227/137
(58) Field of Classification Search .................. 227/120, 227/131, 135, 137, 119, 147; 606/100, 104, 606/99, 95, 279, 329
See application file for complete search history.

(56) References Cited

U.S. PATENT DOCUMENTS

| 3,643,851 A | * | 2/1972 | Green et al. ................... 227/19 |
| 4,013,078 A | | 3/1977 | Field ............................ 128/303 |
| 4,653,486 A | | 3/1987 | Coker .......................... 128/92 |
| 4,884,572 A | * | 12/1989 | Bays et al. .................... 606/139 |
| 4,998,452 A | * | 3/1991 | Blum .......................... 81/57.37 |
| 5,000,165 A | | 3/1991 | Watanabe ..................... 128/69 |
| 5,102,421 A | | 4/1992 | Anspach, Jr. ................ 606/232 |
| 5,156,616 A | | 10/1992 | Meadows et al. ........... 606/232 |
| 5,415,661 A | | 5/1995 | Holmes ........................ 606/69 |

(Continued)

FOREIGN PATENT DOCUMENTS

CH    682450    9/1993

(Continued)

*Primary Examiner* — Todd Manahan
*Assistant Examiner* — Marcela I Shirsat
(74) *Attorney, Agent, or Firm* — Stradley Ronon Stevens & Young, LLP

(57) ABSTRACT

The present invention relates to a surgical method or procedure for securing a prosthesis to bone. More particularly, the present invention relates to (i) a surgical method or procedure for securing a low load bearing prosthesis such as, for example, an adhesion barrier, to a patient's bone, (ii) a tack or drive screw for securing the low load bearing prosthesis and (iii) associated instrumentation for driving the tack or drive screw into the patient's bone.

16 Claims, 16 Drawing Sheets

U.S. PATENT DOCUMENTS

| | | | | |
|---|---|---|---|---|
| 5,437,672 | A | 8/1995 | Alleyne | 606/61 |
| D366,113 | S | 1/1996 | Morgan | D24/145 |
| 5,492,452 | A * | 2/1996 | Kirsch et al. | 411/455 |
| 5,591,169 | A | 1/1997 | Benoist | 606/69 |
| 5,611,354 | A | 3/1997 | Alleyne | 128/846 |
| 5,645,599 | A | 7/1997 | Samani | 623/17 |
| 5,681,310 | A | 10/1997 | Yuan et al. | 606/61 |
| 5,725,582 | A | 3/1998 | Bevan et al. | 623/17 |
| 5,868,745 | A | 2/1999 | Alleyne | 606/61 |
| 5,971,985 | A | 10/1999 | Carchidi et al. | 606/61 |
| 6,039,763 | A | 3/2000 | Shelokov | 623/17 |
| 6,042,534 | A | 3/2000 | Gellman et al. | 600/30 |
| 6,074,419 | A | 6/2000 | Healy et al. | 623/2.14 |
| 6,106,558 | A | 8/2000 | Picha | 623/23.74 |
| 6,127,596 | A | 10/2000 | Brown et al. | 623/16 |
| 6,197,036 | B1 | 3/2001 | Tripp et al. | 606/151 |
| 6,206,882 | B1 | 3/2001 | Cohen | 606/69 |
| 6,221,109 | B1 | 4/2001 | Geistlich et al. | 623/17.11 |
| 6,264,655 | B1 | 7/2001 | Pisharodi | 606/61 |
| 6,280,473 | B1 | 8/2001 | Lemperle et al. | 623/16.11 |
| 6,284,000 | B1 | 9/2001 | Ege | 623/21.11 |
| 6,287,743 | B1 | 9/2001 | Oakland et al. | 430/201 |
| 6,312,469 | B1 | 11/2001 | Gielen et al. | 623/17.11 |
| 6,402,759 | B1 * | 6/2002 | Strong et al. | 606/104 |
| 6,454,767 | B2 | 9/2002 | Alleyne | 606/61 |
| 6,475,219 | B1 | 11/2002 | Shelokov | 606/61 |
| 6,524,312 | B2 | 2/2003 | Landry et al. | 606/61 |
| 6,576,017 | B2 | 6/2003 | Foley et al. | 623/17.16 |
| 6,645,211 | B2 | 11/2003 | Magana | 606/72 |
| 6,652,585 | B2 | 11/2003 | Lange | 623/17.11 |
| 6,673,362 | B2 * | 1/2004 | Calhoun et al. | 424/426 |
| 6,712,851 | B1 | 3/2004 | Lemperle et al. | 623/16.11 |
| 6,723,099 | B1 | 4/2004 | Goshert | 606/72 |
| 6,758,863 | B2 | 7/2004 | Estes et al. | 623/17.16 |
| 6,852,128 | B2 | 2/2005 | Lange | 623/17.11 |
| 6,875,213 | B2 | 4/2005 | Michelson | 606/61 |
| 7,041,138 | B2 | 5/2006 | Lange | 623/17.11 |
| 7,052,497 | B2 | 5/2006 | Sherman et al. | 606/61 |
| 7,074,238 | B2 | 7/2006 | Stinson et al. | 623/17.11 |
| 7,090,698 | B2 | 8/2006 | Goble et al. | 623/17.11 |
| 7,147,641 | B2 * | 12/2006 | Chen | 606/104 |
| 7,163,561 | B2 | 1/2007 | Michelson | 623/17.16 |
| 7,223,289 | B2 | 5/2007 | Trieu et al. | 623/17.11 |
| 7,229,441 | B2 | 6/2007 | Trieu et al. | 606/61 |
| 7,273,497 | B2 | 9/2007 | Ferree | 623/17.16 |
| 7,533,672 | B2 | 5/2009 | Morgan et al. | 128/846 |
| 2003/0078588 | A1 | 4/2003 | Alleyne | 606/86 |
| 2004/0204723 | A1 * | 10/2004 | Kayan | 606/151 |
| 2005/0126576 | A1 | 6/2005 | Ferree | 128/846 |
| 2005/0177155 | A1 | 8/2005 | Alleyne | 606/61 |
| 2005/0273120 | A1 | 12/2005 | Abdou | 606/151 |
| 2006/0014119 | A1 | 1/2006 | Bouneff | 433/118 |
| 2006/0154205 | A1 | 7/2006 | Reggie | 433/173 |
| 2006/0287723 | A1 | 12/2006 | Muhanna et al. | 623/13.14 |
| 2007/0141529 | A1 | 6/2007 | Bouneff | 433/118 |
| 2007/0208346 | A1 | 9/2007 | Marnay et al. | 606/61 |
| 2008/0064010 | A1 | 3/2008 | Ten Bruggenkate | 433/174 |

FOREIGN PATENT DOCUMENTS

| | | |
|---|---|---|
| EP | 0 301 489 | 2/1989 |
| FR | 2 795 621 | 1/2001 |
| FR | 2 850 562 | 8/2004 |
| WO | WO 97/30638 | 8/1997 |
| WO | WO 2007/002012 | 1/2007 |
| WO | WO 2007/002071 | 1/2007 |

* cited by examiner

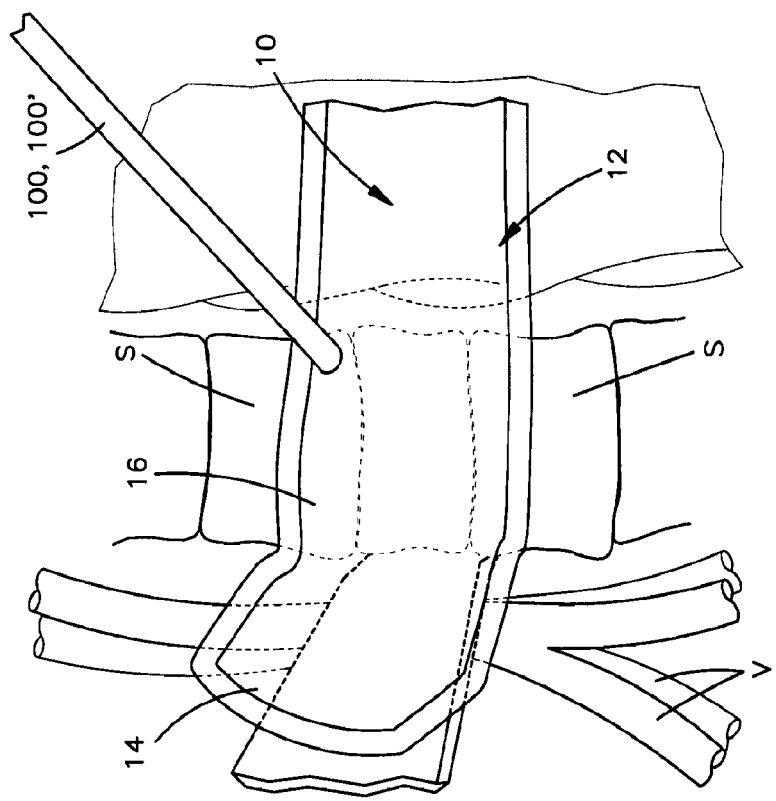
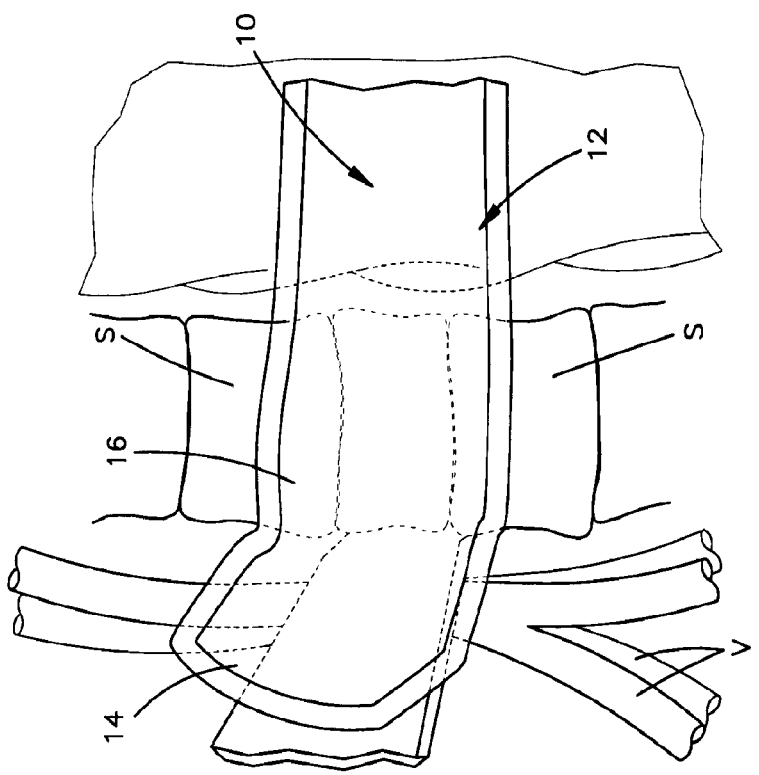
Fig.1B
Fig.1A

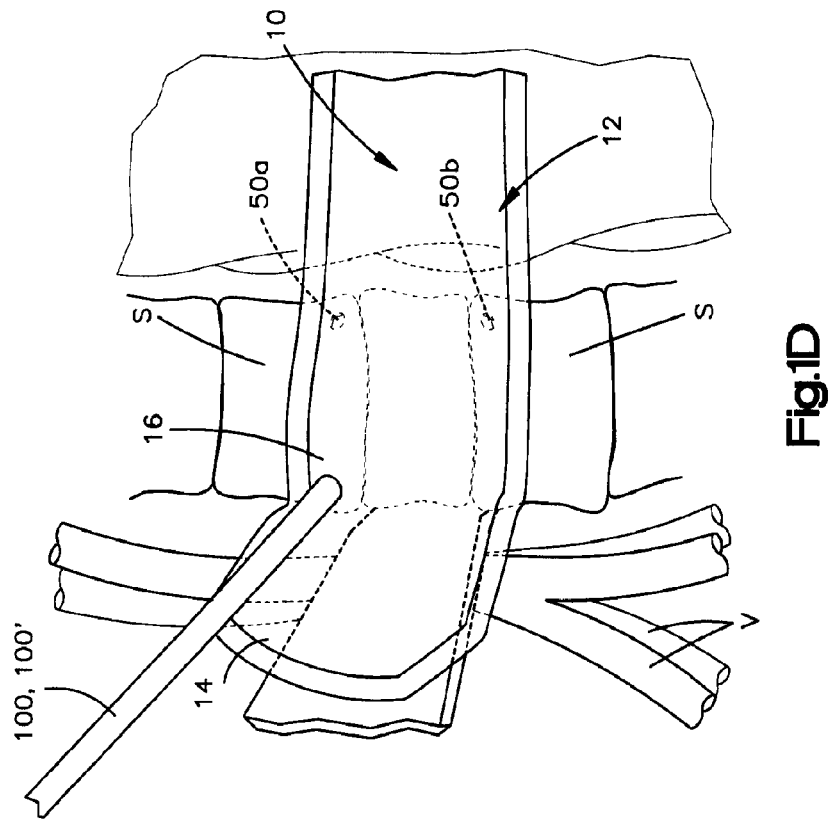
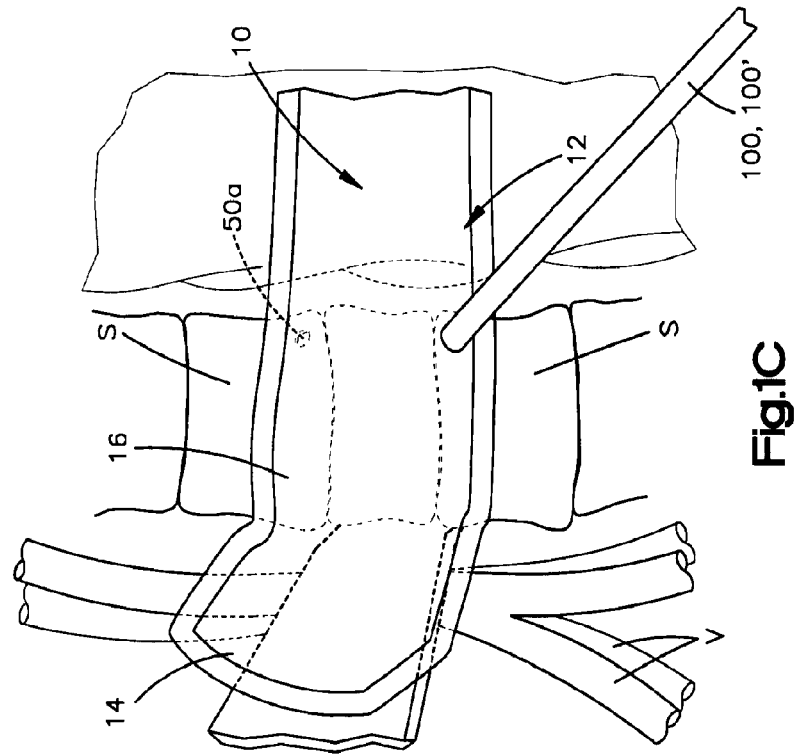

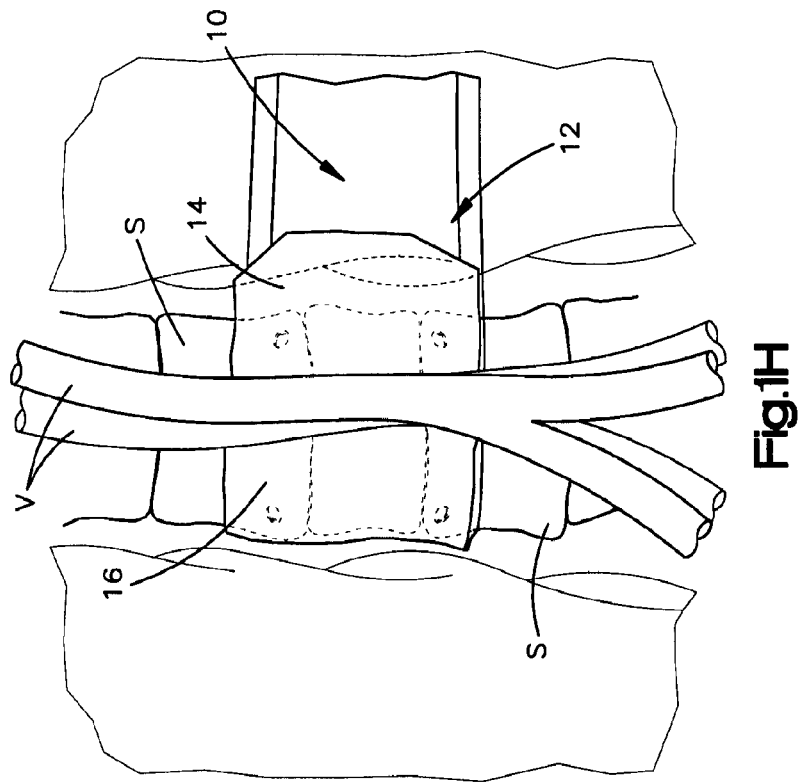
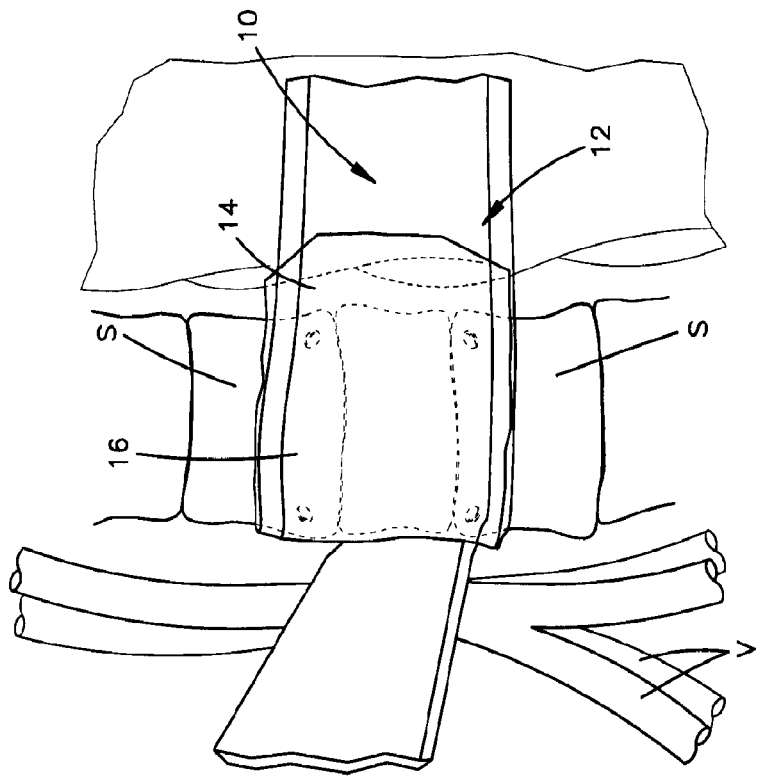

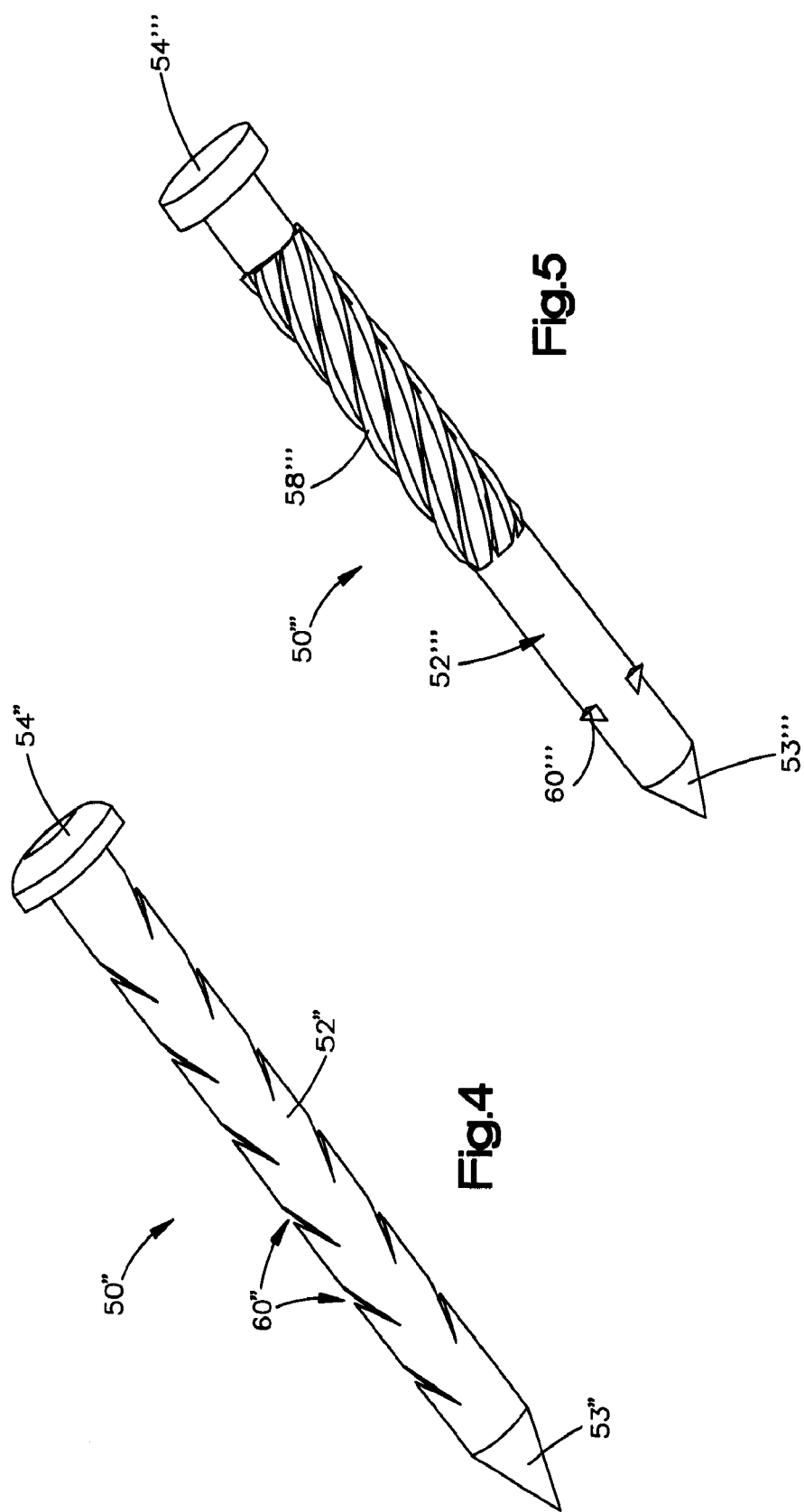

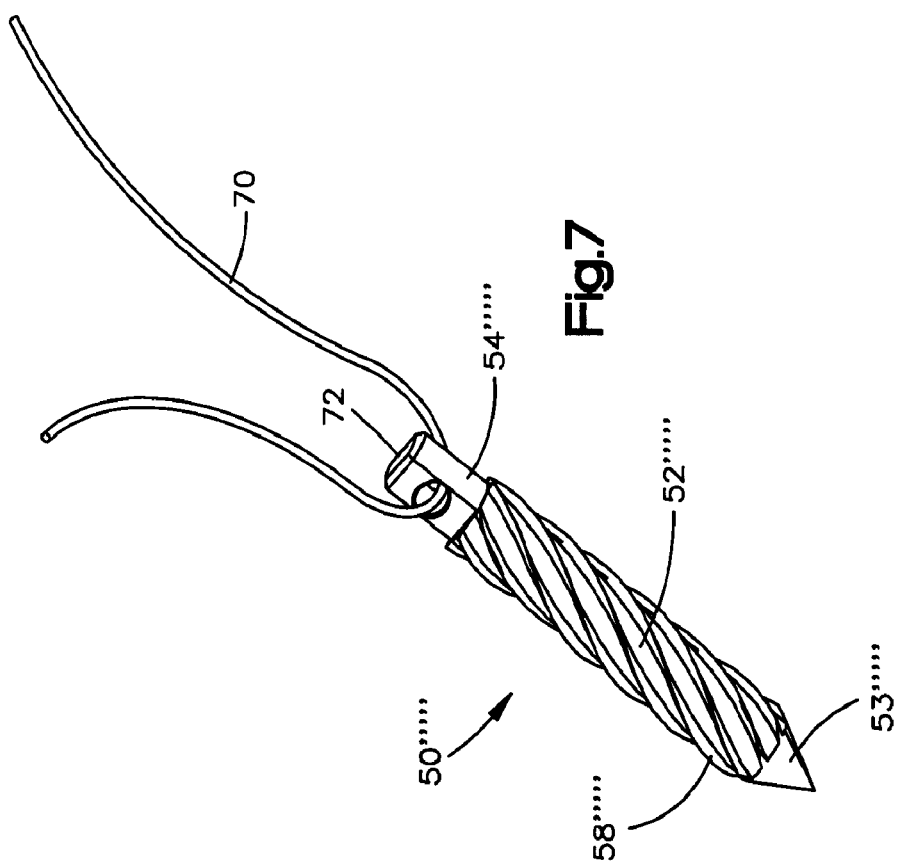
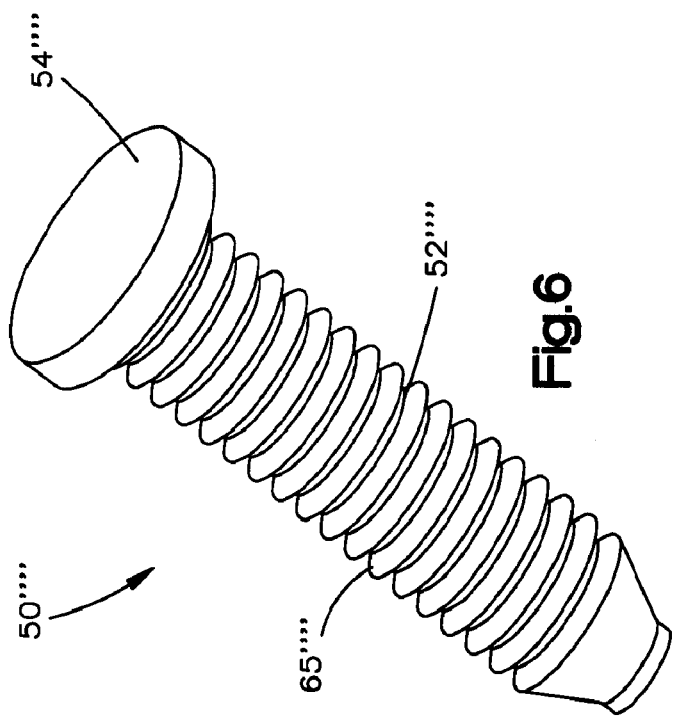

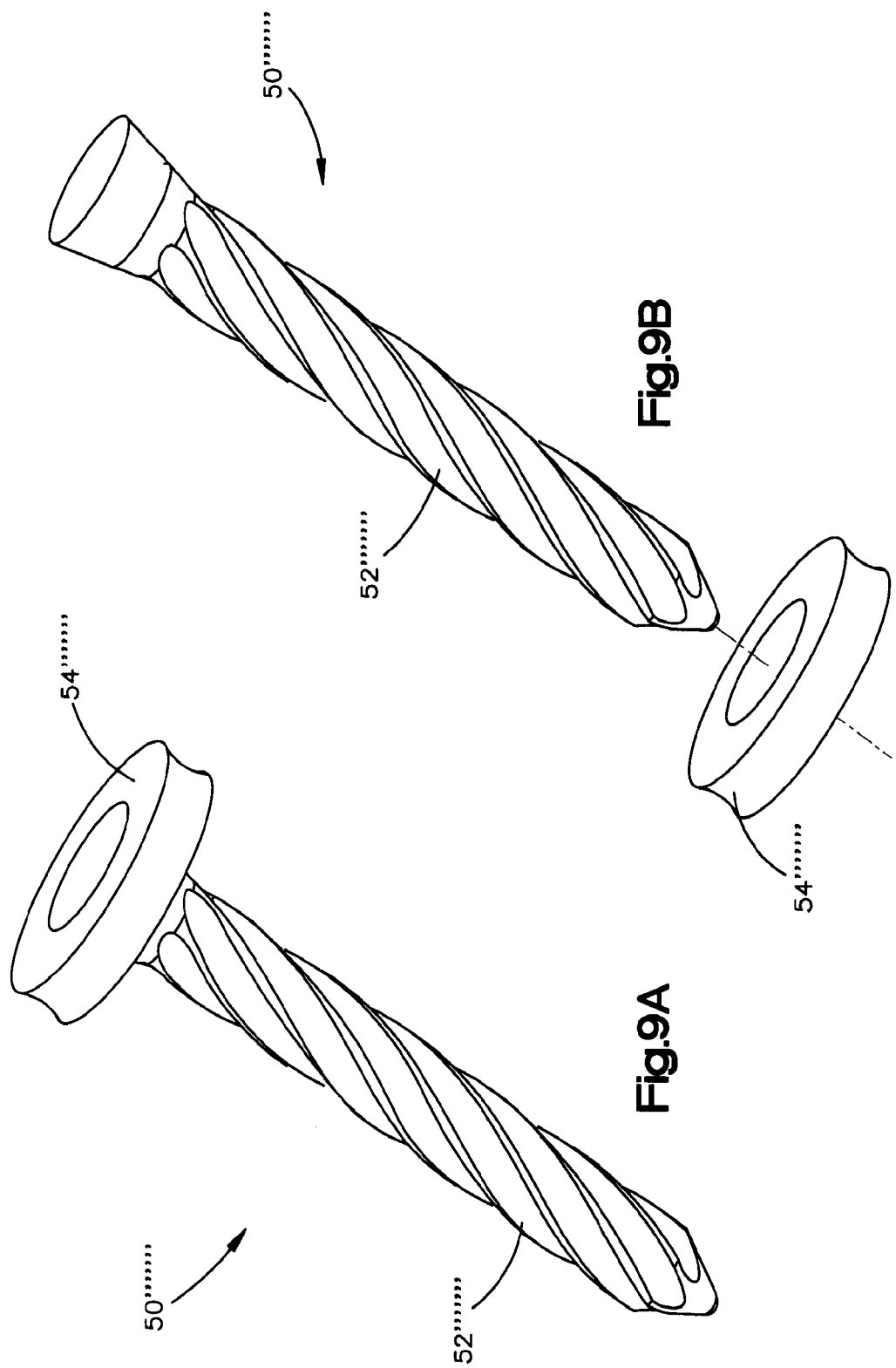

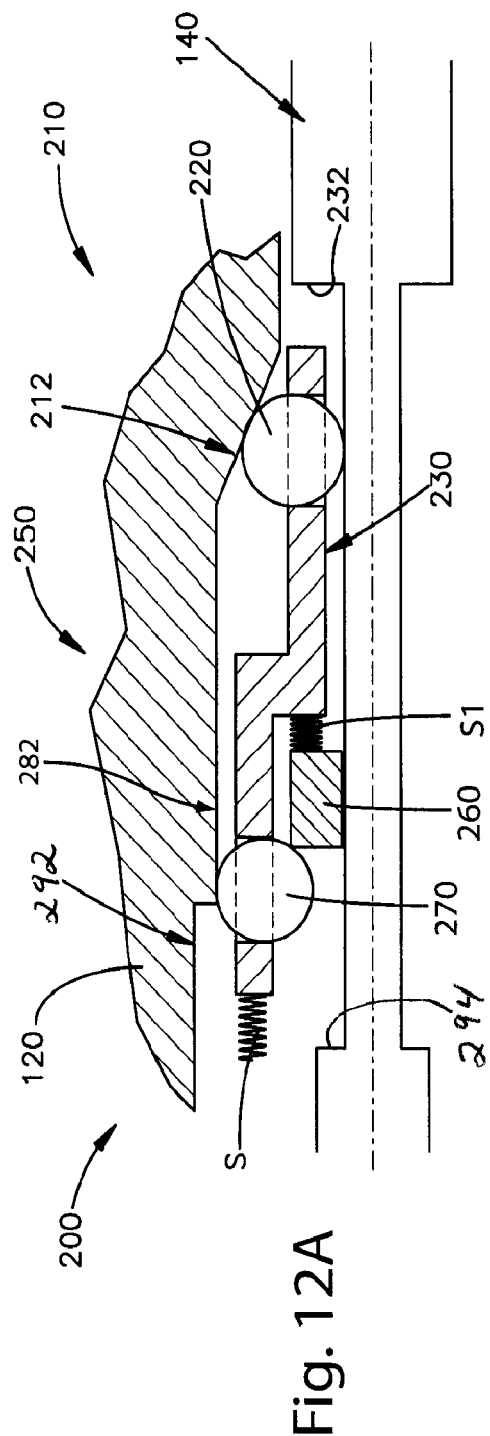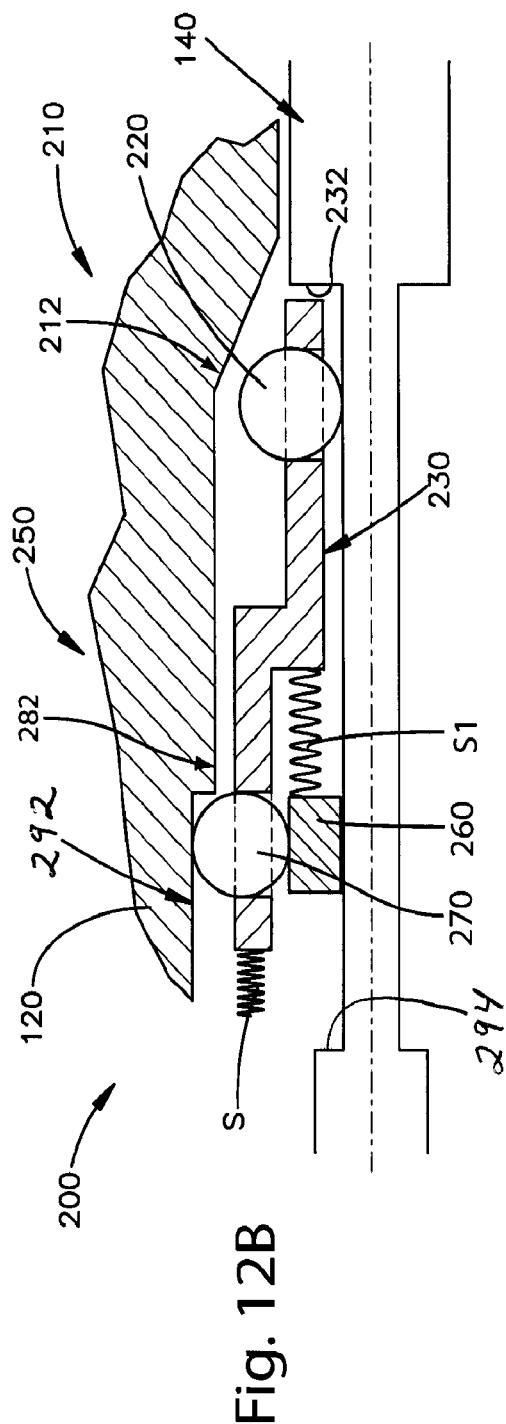
Fig. 12A
Fig. 12B

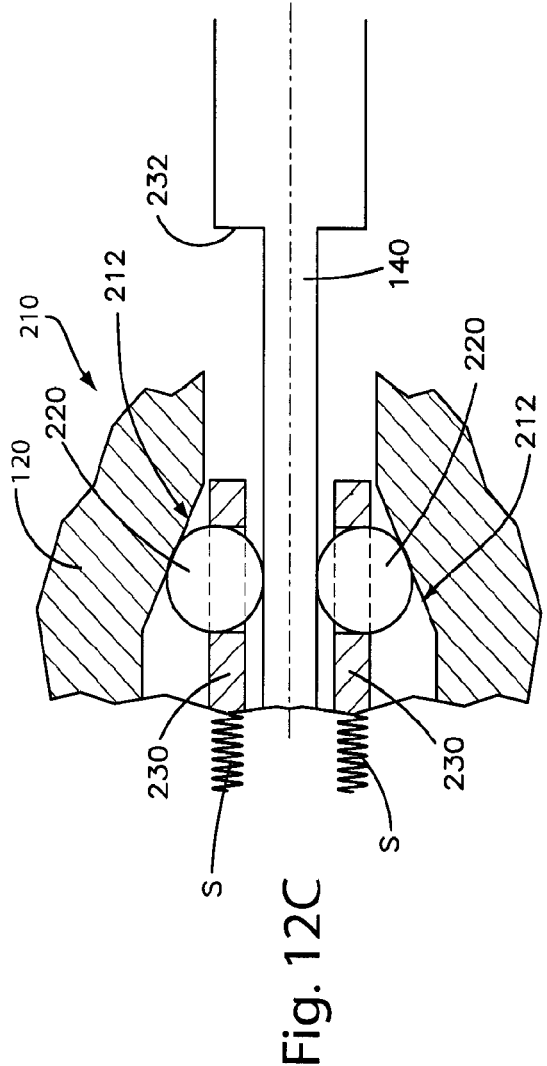
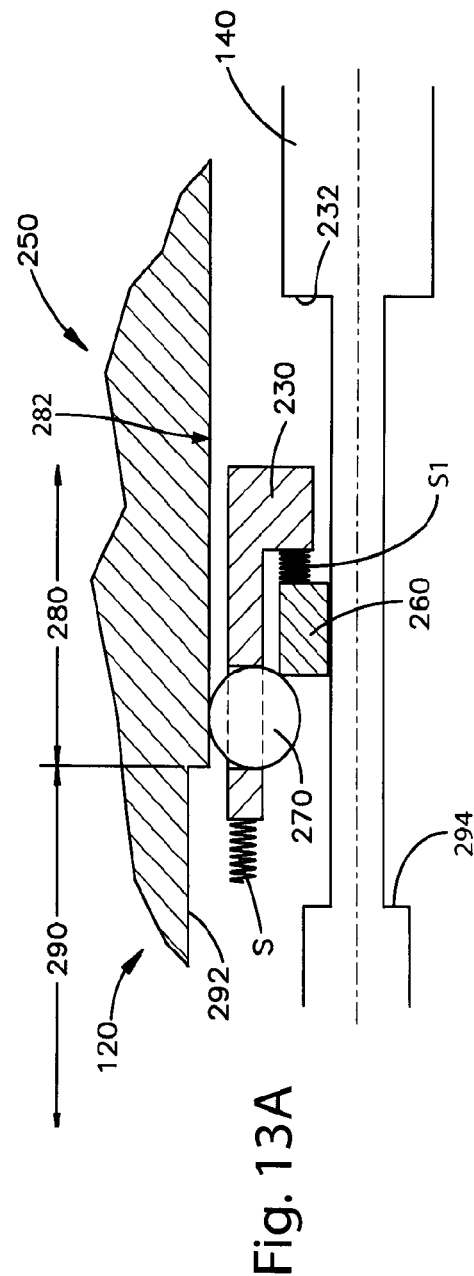

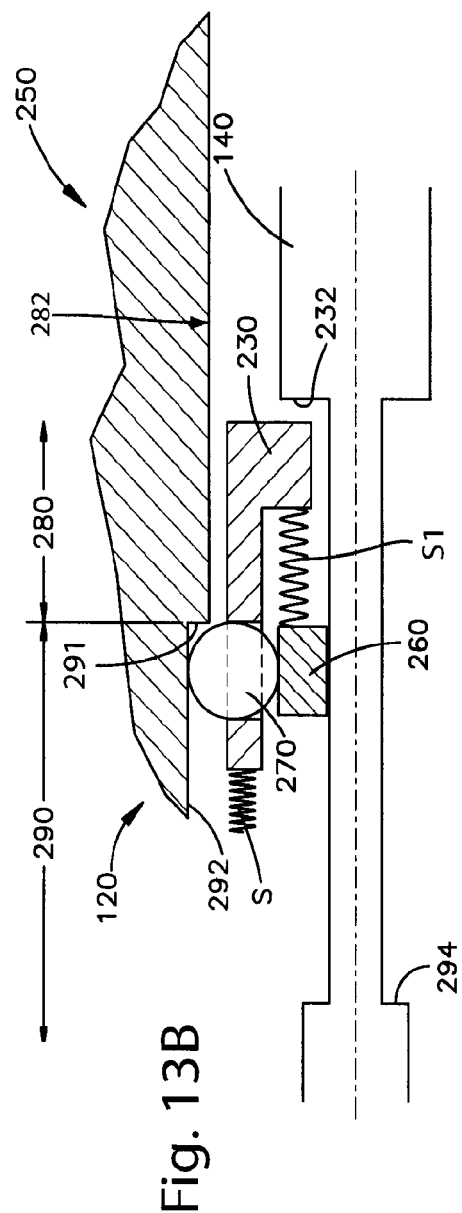
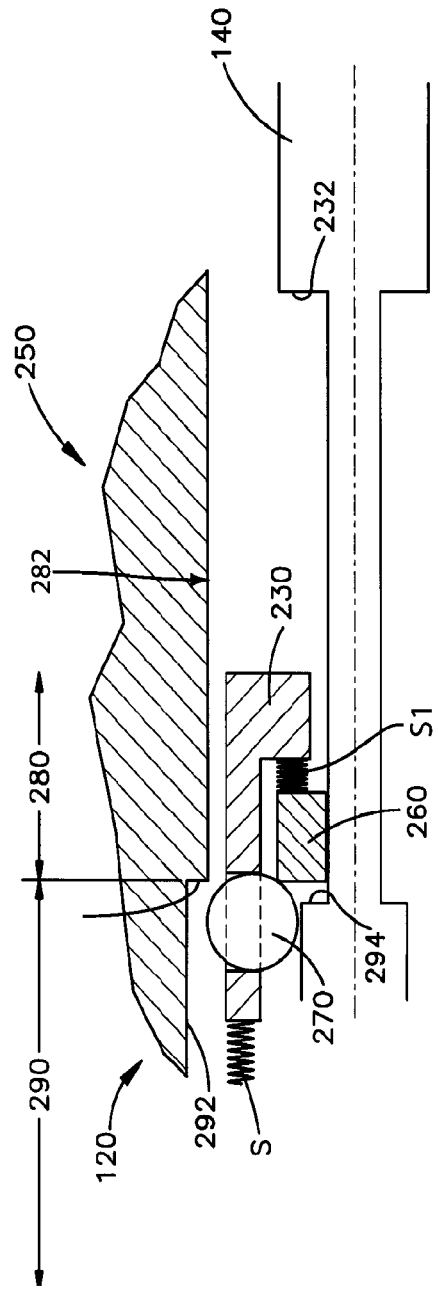
Fig. 13B
Fig. 13C

TACK OR DRIVE SCREW FOR SECURING A PROSTHESIS TO BONE AND ASSOCIATED INSTRUMENTATION AND METHOD

CROSS-REFERENCE TO RELATED APPLICATIONS

This national stage application of PCT/US2008/088462 claims the benefit of U.S. Provisional Application No. 61/017,402, filed on Dec. 28, 2007, entitled "TACK OR DRIVE SCREW FOR SECURING A PROSTHESIS TO BONE AND AN INSTRUMENT FOR IMPLANTING THE SAME," the contents of which is incorporated in its entirety by reference herein.

BACKGROUND OF THE INVENTION

Various surgical procedures including, for example, spinal procedures may include the securement of a low load bearing prosthesis such as, for example, an adhesion barrier, to a patient's bone in order to minimize and/or prevent scar tissue from adhering to one or more tissues, organs, arteries, veins, blood vessels, etc. such as, for example, to the aorta, vena cava and/or other retroperitoneal structures (collectively referred to herein as vessel V). Generally speaking, the low load bearing prosthesis acts as a barrier to prevent scar tissue from adhering to the patient's vessel V. That is, placement of the low load bearing prosthesis between the surgical site and the patient's vessel V helps prevent scar tissue from adhering to the patient's vessel V.

In addition, the low load bearing prosthesis may facilitate identification of surgical planes and/or safe navigation paths around critical vessels V during a revision surgery if one is needed. That is, the low load bearing prosthesis may operate to produce one or more planes through a scar laden field so that a surgeon can navigate along the prosthesis during a subsequent revision surgery if necessary.

As such, low load bearing prosthesis, unlike rigid fixation systems or load bearing prosthesis such as, for example, bone plates, do not carry load while the patient heals or during the patient's lifetime. Thus, the low load bearing prosthesis is often in the form of a thin plate, a membrane or a barrier and only requires appropriate alignment and placement.

Thus, it is advantageous to provide fixation implants, instruments and a surgical method to secure the low load bearing prosthesis to the patient's bone via a plurality of impact driven fixation implants so that overall surgical time is minimized.

BRIEF SUMMARY OF THE INVENTION

The present invention relates to a surgical method or procedure for securing a prosthesis to bone. More particularly, the present invention relates to (i) a surgical method or procedure for securing a low load bearing prosthesis such as, for example, an adhesion barrier, to a patient's bone, (ii) a tack or drive screw for securing the low load bearing prosthesis and (iii) associated instrumentation for driving the tack or drive screw into the patient's bone.

BRIEF DESCRIPTION OF THE DRAWINGS

The foregoing summary, as well as the following detailed description of the preferred embodiments of the application, will be better understood when read in conjunction with the appended drawings. For the purposes of illustrating the surgical method and associated tack and instrumentation of the present application, there are shown in the drawings preferred embodiments. It should be understood, however, that the application is not limited to the precise arrangements and instrumentalities shown. In the drawings:

FIGS. 1A-1H illustrate various plan views of steps of an exemplary surgical method for securing a low load bearing prosthesis to a patient's spine in accordance with one aspect of the preferred invention;

FIG. 4 illustrates a side perspective view of a tack according to a second preferred embodiment of the present invention;

FIG. 5 illustrates a side perspective view of a tack according to a third preferred embodiment of the present invention;

FIG. 6 illustrates a side perspective view of a tack according to a fourth preferred embodiment of the present invention;

FIG. 7 illustrates a side perspective view of a tack according to a fifth preferred embodiment of the present invention;

FIG. 9A illustrates a side perspective view of a tack according to a seventh preferred embodiment of the present invention;

FIG. 9B illustrates an exploded, side perspective view of the tack illustrated in FIG. 9A;

FIG. 12A is a cross-sectional view of an automatic resetting mechanism which may be used in conjunction with the insertion instrument of FIG. 10, the automatic resetting mechanism illustrated in its initial position;

FIG. 12B is a cross-sectional view of the automatic resetting mechanism illustrated in FIG. 12A, the automatic resetting mechanism illustrated in a second, disassociated position;

FIG. 12C is a magnified cross-sectional view of a unidirectional braking mechanism of the automatic resetting mechanism illustrated in FIG. 12A, the unidirectional braking mechanism illustrated in its initial position;

FIG. 13A is a magnified cross-sectional view of a position locking mechanism of the automatic resetting mechanism illustrated in FIG. 12A, the position locking mechanism illustrated in its initial position;

FIG. 13B is a magnified cross-sectional view of the position locking mechanism of the automatic resetting mechanism illustrated in FIG. 12A, the position locking mechanism illustrated in a second position;

FIG. 13C is a magnified cross-sectional view of the position locking mechanism of the automatic resetting mechanism illustrated in FIG. 12A, the position locking mechanism illustrated moving from the second position to the initial position;

DETAILED DESCRIPTION OF THE INVENTION

Figure 1F:
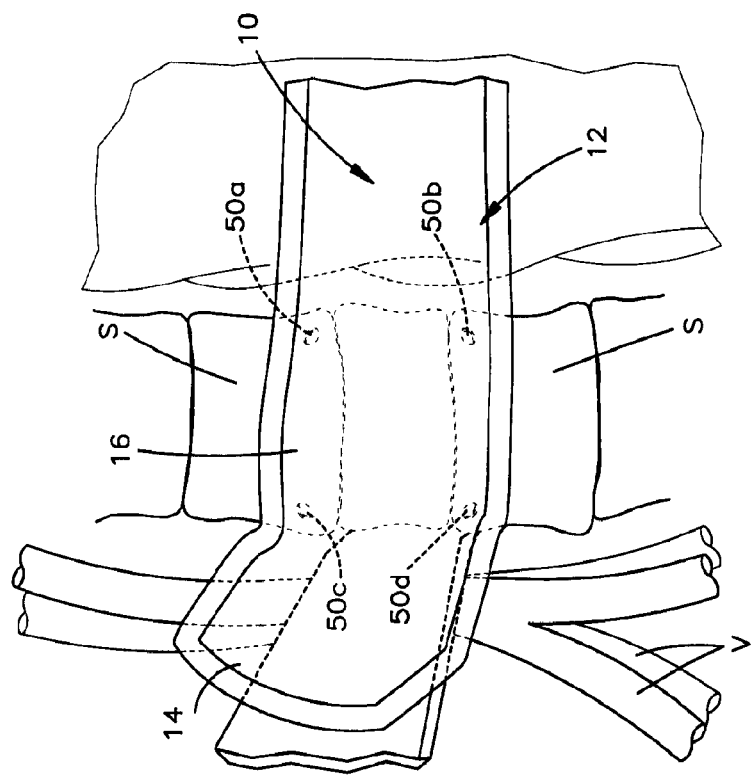

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, the present invention is directed to a surgical method or procedure for securing a low load bearing prosthesis 10 to a patient's bone. More specifically, preferred embodiments of the present invention are directed to a surgical method or procedure for securing a low load bearing prosthesis 10 to one or more vertebral bodies in a patient's spine S to minimize or substantially prevent scar tissue from adhering to surrounding vessels V. The low load bearing prosthesis 10 may also provide a plane of dissection during a revision surgery, if necessary. The present invention is also directed to various exemplary embodiments of a tack or drive screw (collectively referred to herein as a tack) 50 and associated instrumentation 100, 100', 300, 400 for driving the tack 50 into the patient's vertebral bodies to secure the low load bearing prosthesis 10 to the patient's spine S. The tack 50 is configured to be impact driven via a hammering type or push action as opposed to a rotating type action into the patient's spine S.

As will be described in greater detail below, while the preferred tack 50, instrumentation 100, 100', 300, 400 and surgical method or procedure of the present invention is used for securing a low load bearing prosthesis 10 to the spine of a patient, it will be generally understood by one of ordinary skill in the art, that the tack 50, instrumentation 100, 100', 300, 400 and surgical method or procedure may be equally applicable in other surgical procedures in which a surgeon desires to secure a prosthesis 10 to bone including, but not limited to, for use in trauma surgery, cranial maxio-facial surgery, plastic and reconstructive surgery, etc. Preferred embodiments of the present invention may also have some applicability to securing larger load bearing prosthesis (e.g., bone plate) to bone.

In use, as will be described in the greater detail below, the low load bearing prosthesis 10 preferably protects a surgical site from the development of scar tissue that may adhere to a patient's surrounding vessel V following a surgical procedure. That is, the low load bearing prosthesis 10 preferably acts as a barrier between the surgical site and one or more of the patient's vessels V in order to minimize and/or prevent scar tissue from adhering to the patient's vessel V. In this manner, the low load bearing prosthesis 10 may be in the shape of a square, rectangle, circle, etc.

In addition, the low load bearing prosthesis 10 may guide a surgeon during a revision surgery through scar laden tissue. The low load bearing prosthesis 10 facilitates identification of surgical planes and/or safe navigation paths around critical vessels V. The low load bearing prosthesis 10 preferably operates to produce one or more planes through a scar laden field so that the surgeon can navigate along the prosthesis 10 during a subsequent revision surgery. Thus, the low load bearing prosthesis 10 functions as a barrier for vessels V following, for example, an anterior vertebral surgery, to reduce the risk of potential vessel V damage during a revision surgery by providing a plane of dissection.

Figure 2:
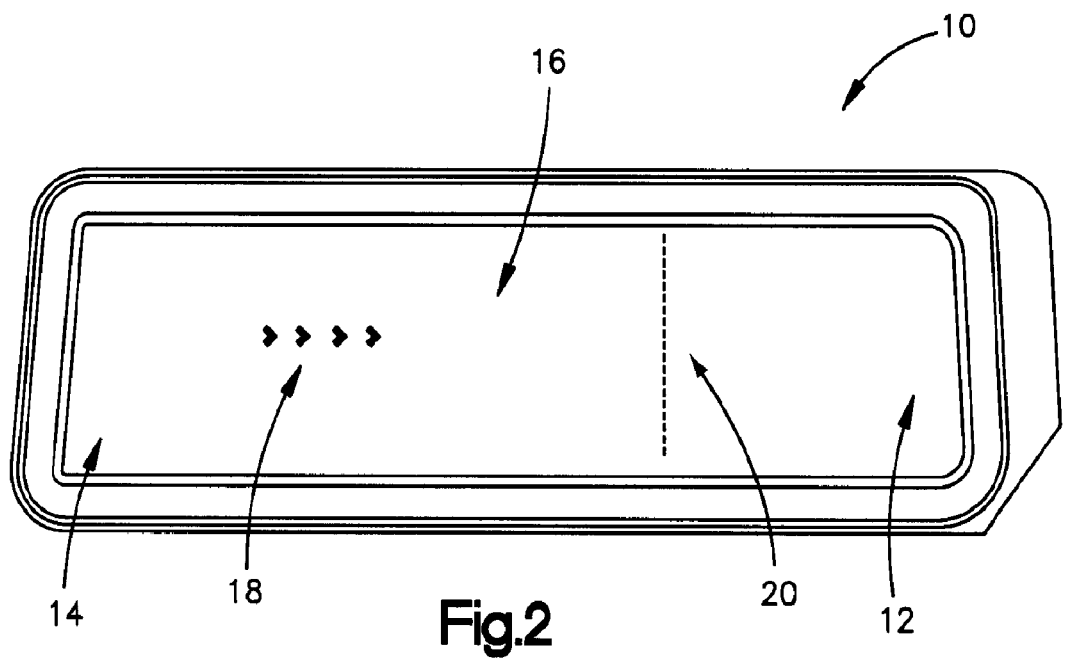
FIG. 2 illustrates a top plan view of an exemplary low load bearing prosthesis that may be utilized with the preferred methods and instruments of the present invention.

Generally, the low load bearing prosthesis 10 may be a flexible fabric, barrier or membrane, a thin metal plate, a flat sheet type prosthesis, pliable implants that are used as coverings or scaffolds to protect and function between bone, vertebral bodies, and surrounding vessel V, prosthesis for fixing small bone fragments, scaffold type prosthesis designed to optimize tissue in growth, adhesion barrier type prosthesis to prevent tissue in-growth, prosthesis for holding small bone fragments, small tendons and/or soft tissues in place, etc. Preferably, as disclosed in co-pending International Patent Application No. PCT/US08/88444, filed on Dec. 29, 2008, entitled "A METHOD OF FORMING AND THE RESULTING MEMBRANE COMPOSITION FOR SURGICAL SITE PRESERVATION," the contents of which is incorporated in its entirety by reference herein, and as generally shown in FIG. 2, the low load bearing prosthesis 10 is a hydrogel coated mesh. Preferably, the low load bearing prosthesis 10 includes a first end 12, a second end 14 and an intermediate portion 16. The prosthesis 10 may also include one or more radiopaque indicators 18 and/or one or more pre-form fold lines 20.

As described in U.S. patent application Ser. No. 11/219, 966 entitled "Methods and Apparatus for Vascular Protection in Spinal Surgery," the contents of which is incorporated in its entirety by reference herein, various surgical procedures to access the anterior spinal column have been developed. Such procedures have permitted surgeons to perform repair and corrective surgeries on various parts of the spinal column, such as repairing the motion segments of the spine S. Traditional surgical approaches, for example, to a site in the anterior lumbar region of the spine S entail forming an entry incision through the patient's fascia and through or around one or more muscle planes. Exposure of the affected spinal site also involves movement of the patient's vessels V that lay immediately in front (anterior) of, for example, the lumbar region of the spine S. For example, removal of a degenerative disc and replacement with a fusion cage or prosthesis requires movement of the vessels V for exposure of the intervertebral disc space. The vessels V are then allowed to return to their original position after the spinal procedure has been completed. Depending on the anatomical location of the surgical site, scar tissue may adhere to the surrounding vessel V.

Normally postoperative scar tissue adheres to the vessels V surrounding the patient's spine S and spinal tissue obscures the vessels V as well as other key anatomical landmarks. Due to the lack of visibility in identifying the anatomical landmarks, the resultant scar tissue often produces a nearly blind navigational field during a revision surgery. As such, the resultant scar tissue may become problematic during the revision surgery. While any surgery of the anterior spine requires, as a primary effort, great care in identifying key anatomical landmarks, anterior revision surgery requires navigation (often blindly) through varying degrees of tenacious scar tissue. Identifying vascular structures and other key landmarks to safely commence the revision surgery poses a significant risk to injuring sensitive structures, particularly the vascular anatomy.

As revision surgery is likely to be required for a certain number of patients receiving anterior spinal surgery, there are needs in the art for new methods and apparatus for protecting vascular structures during surgical procedures, particularly revision anterior surgery to the spine S.

Referring to FIGS. 1A-1H, in accordance with the preferred surgical method or procedure of the present invention, a low load bearing prosthesis 10 is secured to the patient's spine S via one or more tacks 50 prior to closing the entry incision. The tack 50 is shown generically in FIGS. 1A-1H and various preferred embodiments of the tack 50 are shown in FIGS. 3-9B with multiples of prime symbols (') to identify the various embodiments. Under conventional surgical procedures, the surgeon typically begins closing procedures after the patient's spine has been repaired. However, in accordance with the present invention, the surgeon will first implant the low load bearing prosthesis 10 via one or more tacks 50 so that once implanted, the low load bearing prosthesis 10 operates, at least in part, to prevent scar tissue from adhering to the patient's vessels V and/or to assist a surgeon in a subsequent surgery, if necessary, to the same motion segment.

Figure 1E:
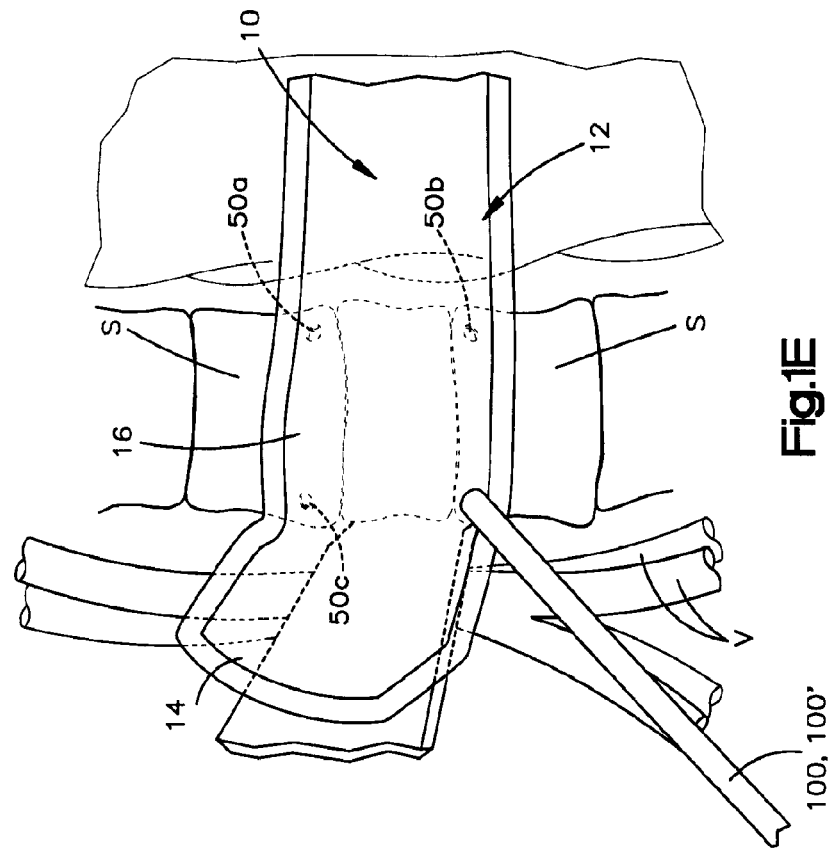

As shown in FIG. 1A, the prosthesis 10 is placed over at least a portion of the surgical repair site. Thereafter, as shown in FIGS. 1B and 1C, a first end 12 of the prosthesis 10 is tacked to at least one vertebral body in the patient's spine S via one or more impact driven tacks 50, as will be described in greater detail below. More preferably, a first tack 50a is used to attach the prosthesis 10 to a first vertebral body, while a second tack 50b is used to attach the prosthesis 10 to a second, adjacent vertebral body. The prosthesis 10 is then tacked to the first and second vertebral bodies at an intermediate portion 16 of the prosthesis 10 by third and fourth tacks 50c, 50d, respectively, as shown in FIGS. 1D and 1E. Referring to FIGS. 1F and 1G, the prosthesis 10 is then preferably folded at least partially over itself one or more times along one or more fold lines 20. In this regard, the surgeon may determine the one or more fold positions, intermediate to the first and second ends 12, 14, based on the patient's anatomy. Alternatively or in addition, the prosthesis 10 may include one or more visual, pre-formed fold lines 20 suggesting to the surgeon where to fold the prosthesis 10 to accommodate a suitable implantation position.

The second end 14 of the prosthesis 10 preferably extends away from the patient's spine S and preferably is coupled to a structure of the patient spaced in a direction away from the patient's spine S towards the entry incision. For example, the second end 14 of the prosthesis 10 may be coupled to the posterior rectus sheath, the psoas muscle, etc. via, for example, a suture, a clip, etc.

Once implanted, the prosthesis 10 lays nascent until a revision procedure is performed. During a revision surgery, the prosthesis 10 permits the surgeon to reduce possible complications associated with scar related navigational errors to the original surgical site.

The prosthesis 10 preferably also includes one or more radiopaque indicators 18 that preferably enable the use of a machine to read and/or locate the one or more indicators 18 prior to and/or during the revision surgery for localization and re-entry into the prior surgical site. Preferably, the one or more radiopaque indicators 18 are disposed proximate the second end 14 of the prosthesis 10 so that the surgeon may identify the location of the second end 14 before an incision procedure.

Irrespective of whether machine radiopaque indicators 18 are employed, the reentry procedure preferably includes utilizing the prior entry incision, the previous fascia incision, and location of the second end 14 of the prosthesis 10. Next, the surgeon preferably dissects down along the prosthesis 10, which identifies sensitive anatomical structure(s), surgical planes and safe navigation path(s) around critical vessels V and through scar laden areas.

Upon re-entry to the site, the prosthesis 10 may be pulled in an anterior direction so that the prosthesis 10 may unfold in the manner of an accordion and expose the site. Thus, the surgeon may carefully unwrap or pull the prosthesis 10 away from the spine S to expose the site. Vessel V refraction, removal of the prosthesis 10, and the revision surgery on the spine S may then take place. After the revision surgery to the spine S is complete, a new prosthesis 10 may be implanted utilizing the techniques discussed above.

Exemplary Embodiments of Tacks

In general, referring to FIGS. 3-9B, the tack 50 is preferably configured to be impact driven into the patient's bone via a hammering type motion as opposed to being rotated into engagement with the patient's bone. Preferably, the tack 50 can be delivered via one or multiple impact-type driving actions. The tack 50 preferably includes a head portion 54 and a shaft portion 52. The head portion 54 may include a drive mechanism 56 for facilitating removal of the tack 50 from the patient's bone via a removal instrument (not shown), if necessary. The shaft portion 52 may include a sharp distal point 53 and a relatively small outer diameter to facilitate driving the tack 50 into the patient's spine S without pre-drilling.

In use, the tack 50 of the present invention preferably incorporates one of two design principles that allow the tack 50 to be impact driven into the patient's bone. The first design principle is that the tack 50 includes an external flange 58 extending from an outer surface of the tack 50 so that the tack 50 partially rotates as the tack 50 is being driven into the patient's bone (e.g., similar to a helical blade). The second design principle is that the tack 50 may incorporate one or more barbs 60 that can be impact driven in one direction, but resist motion in the opposite direction. The barbs 60 can be patterned in a variety of manners around, up and down the length of the tack 50.

Preferably the tack 50 has a diameter of about three and one-half millimeters (3.5 mm) or smaller. More preferably, the tack 50 has an outer diameter of about one and two tenths millimeters (1.2 mm) to about one and eight tenths millimeters (1.8 mm). If the tack 50 incorporates a flange 58, the flange 58 preferably has a height of about one tenth of a millimeter (0.1 mm) to about one-half millimeter (0.5 mm) and a length of about three millimeters (3 mm) to about sixteen millimeters (16 mm). However, the tack 50 is not limited to any of the above-listed preferred dimensions and may have nearly any size and shape that is preferred for a specific patient and/or procedure.

Figure 3:
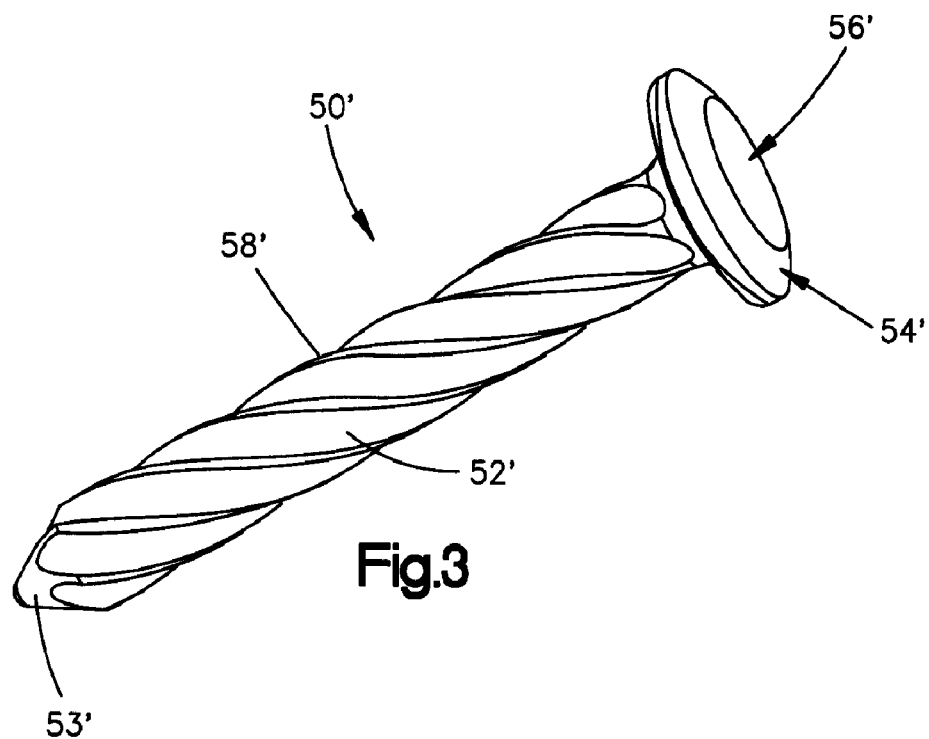
FIG. 3 illustrates a side perspective view of a tack according to a first preferred embodiment of the present invention.

Referring to FIG. 3, the first preferred embodiment of the tack 50' for use with the present invention is preferably in the form of a spiral tack 50'. The spiral tack 50' includes a head portion 54' and a shaft portion 52'. The head portion 54' includes a drive mechanism 56' for facilitating removal of the spiral tack 50' from the patient's bone via a removal instrument (not shown), if necessary. The shaft portion 52' includes a sharp distal point 53' and a small outer diameter to facilitate the spiral tack 50' being impact driven into the patient's vertebral bodies without pre-drilling. The spiral tack 50' also preferably includes an external flange 58' extending from an outer surface of the tack 50'. The flange 58' preferably has a large flange pitch that enables the spiral tack 50' to be driven into the vertebral bodies via a direct axial impact (e.g., via a hammering action). The flange pitch however is configured such that the spiral tack 50' rotates as it is being impact driven into the patient's bone. The spiral tack 50' may contain one to seven flange revolutions, although any other number of revolutions is envisioned so long as the spiral tack 50' is capable of rotating to limit bone splitting as the spiral tack 50' is being impact driven into the patient's bone. Preferably, the spiral tack 50' includes a flange pitch that allows the spiral tack 50' to rotate from about thirty degrees) (30°) to about three hundred sixty degrees (360°).

Referring to FIG. 4, the second preferred embodiment of the tack 50" for use with the present invention is preferably in the form of a barbed tack 50". The barbed tack 50" preferably includes one or more barbs 60" formed on an external surface of the tack 50" in order to prevent pullout. Preferably, the one or more barbs 60" are cut into the tack 50". In addition, the barbs 60" can be staggered to help with alignment in a cartridge, as will be described in greater detail below.

Referring to FIG. 5, the third preferred embodiment of the tack 50''' for use with the present invention includes a partial flange 58''' combined with one or more barbs 60'''. That is, the tack 50''' preferably includes an external flange 58''', as described in conjunction with the first preferred embodiment, and one or more barbs 60''', as described in conjunction with the second preferred embodiment, thus enabling the tack 50''' to be impact driven into the patient's bone. As shown, the one or more barbs 60''' are preferably located distally of the partial external flange 58''' so that the barbs 60''' engage the bone prior to the flange 58'''. Alternatively, the partial external flange 58''' may be located distally of the barbs 60'''.

Referring to FIG. 6, the fourth preferred embodiment of the tack 50'''' for use with the present invention may include one or more axial ribs 65'''' to resist pullout. The axial ribs 65 preferably operate similar to the barbs 60, as described above.

Referring to FIG. 7, the fifth preferred embodiment of the tack 50''''' for use with the present invention is preferably in the form of a suture anchor 50'''''. That is, the head portion 54''''' of the tack 50''''' is preferably modified to accept a suture 70. The head portion 54''''' also preferably includes an impact surface 72 so that, in use, the suture anchor 50''''' can be impact driven into the patient's bone. The shaft portion 52''''' preferably includes one or more flanges 58 and/or barbs 60, as previously described.

Figures 8A, 8B:
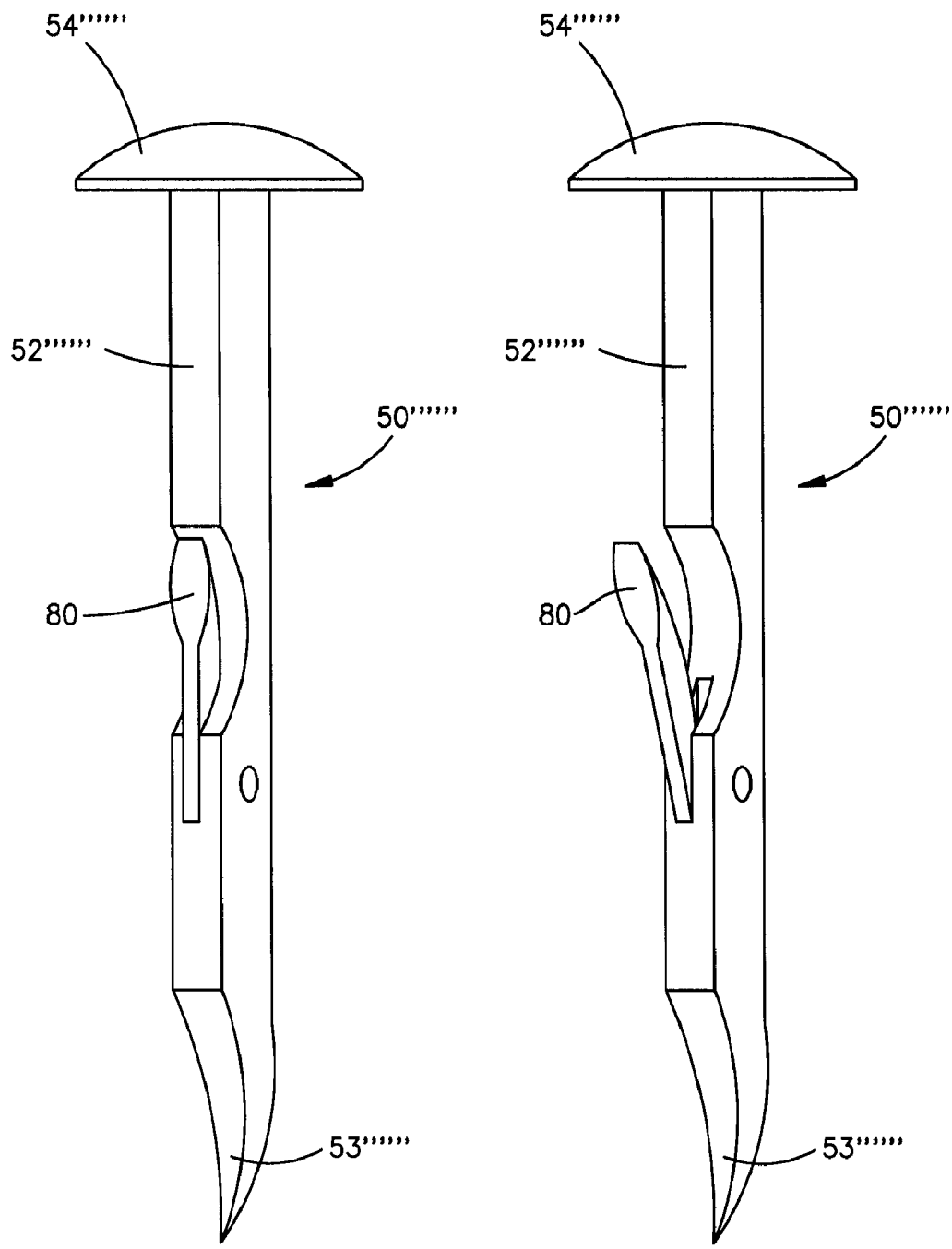
FIG. 8A illustrates a side perspective view of a tack according to a sixth preferred embodiment of the present invention, the tack being in the first, insertion configuration.
FIG. 8B illustrates a side perspective view of the tack illustrated in FIG. 8A, the tack being in a second, deployed configuration.

Referring to FIGS. 8A and 8B, the sixth preferred embodiment of the tack 50'''''' for use with the present invention preferably includes a deployable latch 80. That is, during impaction of the tack 50'''''', the latch 80 is in a first, insertion configuration wherein the latch 80 is preferably contained within or substantially adjacent to the shaft portion 52'''''' of the tack 50''''''. Once impacted, the latch 80 preferably moves to a second, deployed configuration wherein the latch 80 extends from the shaft portion 52'''''' so that the latch 80 resists pullout by obtaining additional bone purchase. The latch 80 may include a spring element (not shown) to assist in deployment. The tack 50'''''' may contain one or more latches 80.

Referring to FIGS. 9A and 9B, the seventh preferred embodiment of the tack 50''''''' for use with the present invention preferably includes a detachable head portion 54'''''''. That is, the tack 50''''''' preferably includes a shaft portion 52''''''' and a head portion 54''''''', wherein the head portion 54''''''' is detachable from the shaft portion 52''''''' so that, in use, the shaft portion 52''''''' can be closely constrained during implantation via a cannulated shaft. As will be described in greater detail below, in situations where the tack 50''''''' is impact driven down a cannulated instrument or shaft, the inner diameter of the cannulated instrument or shaft preferably matches the outer diameter of the tack 50''''''' as much as possible, in order to minimize or prevent misalignment of the tack 50''''''' inside of the cannulated instrument or shaft. Generally, this misalignment is caused by the difference in diameters between the head portion 54''''''' and the shaft portion 52''''''' of the tack 50'''''''. The greater the size difference, the greater the amount of misalignment the tack 50''''''' can encounter, because the inner diameter of the cannulated instrument or shaft is large enough to receive the outer diameter of the head portion 54''''''' of the tack 50'''''''. This, however, enables the shaft portion 52''''''' to move within the cannulated instrument or shaft, thus increasing the likelihood of misalignment. By providing a detachable head portion 54''''''', the cannulated instrument or shaft may have an inner diameter that substantially matches the outer diameter of the shaft portion 52''''''' of the tack 50'''''''. In use, the head portion 54''''''' may be placed at the distal end of the cannulated instrument or shaft, in-between the distal end of the cannulated instrument or shaft and the prosthesis 10 so that the shaft portion 52''''''' is impact driven from the cannulated instrument or shaft through the head portion 54''''''' and into engagement with the patient's bone. The shaft portion 52''''''' may contain one or more features, such as, an external flange 58 (as shown) for facilitating rotation and/or one or more barbs 60, ribs 65, or deployable latches 80 for resisting pullout.

The tack 50 may be manufactured by any method now or hereafter known including, but not limited to, by heading, thread rolling, milling, etc. The barbs 60 and/or ribs 65 may be manufactured by cutting, machining, etc. The tack 50 may be manufactured from any biocompatible material including, but not limited to, stainless steel, titanium, titanium alloys, bone, including allograft bone, one or more polymers such as, for example, polyetheretherketone (PEEK), poly-1-lactides (PLLA), memory shaped alloys such as Nitionol, one or more bioresorbable material such as, for example, poly-lactic-acid (PLA), etc. The tack 50 may also be coated such as, for example, by a hydroxyapatite to promote bone in-growth or be treated for bone incorporation such as, for example, by plasma coating, etc. Alternatively and/or in addition, the tack 50 may be surfaced finished by, for example, bead blasting to increase pullout strength. Alternatively or in addition, a surgical adhesive may be applied to the tack 50 to improve pullout strength and surface treatments may also be applied that prevent infection or allow for antibiotic surface attachment.

Exemplary Embodiment of the Insertion Instrument for Driving the Tack into the Patient's Bone.

The present invention is also preferably directed to an insertion instrument 100, 100' for driving the tack 50 into the patient's bone. As will be described in greater detail below, the insertion instrument 100, 100' is preferably capable of receiving an impaction force F, which in turn moves an internal piston 140, 140' distally into engagement with the tack 50 so that the tack 50 can be driven into the patient's bone. The impaction force F can be generated by a surgeon's hand, a hammer or mallet, automatically like a nail gun or automated tack driver, etc.

The insertion instrument 100, 100' preferably (i) provides proper alignment and positioning of the tack 50; (ii) reduces or prevents the likelihood of miss-hitting the tack 50 which limits skiving and off-centered bone impact; (iii) reduces or prevents buckling of the tack 50; and (iv) directs the load onto the tack 50 in a manner that optimizes implantation of the tack 50 into the patient's bone. Preferably, the footprint of the insertion instrument 100 is designed such that any additional impact is distributed across the surface of the prosthesis 10 to minimize damage to the underlying bone, tissue, or prosthesis

10. The insertion instrument 100, 100' is preferably designed to position the head 54 of the tack 50 into the vertebral bodies to a precise depth or to position the head 54 a precise height above the prosthesis 10. That is, the internal piston 140, 140' preferably stops at a predetermined point to deliver the tack 50 to a desired depth.

Figure 10:
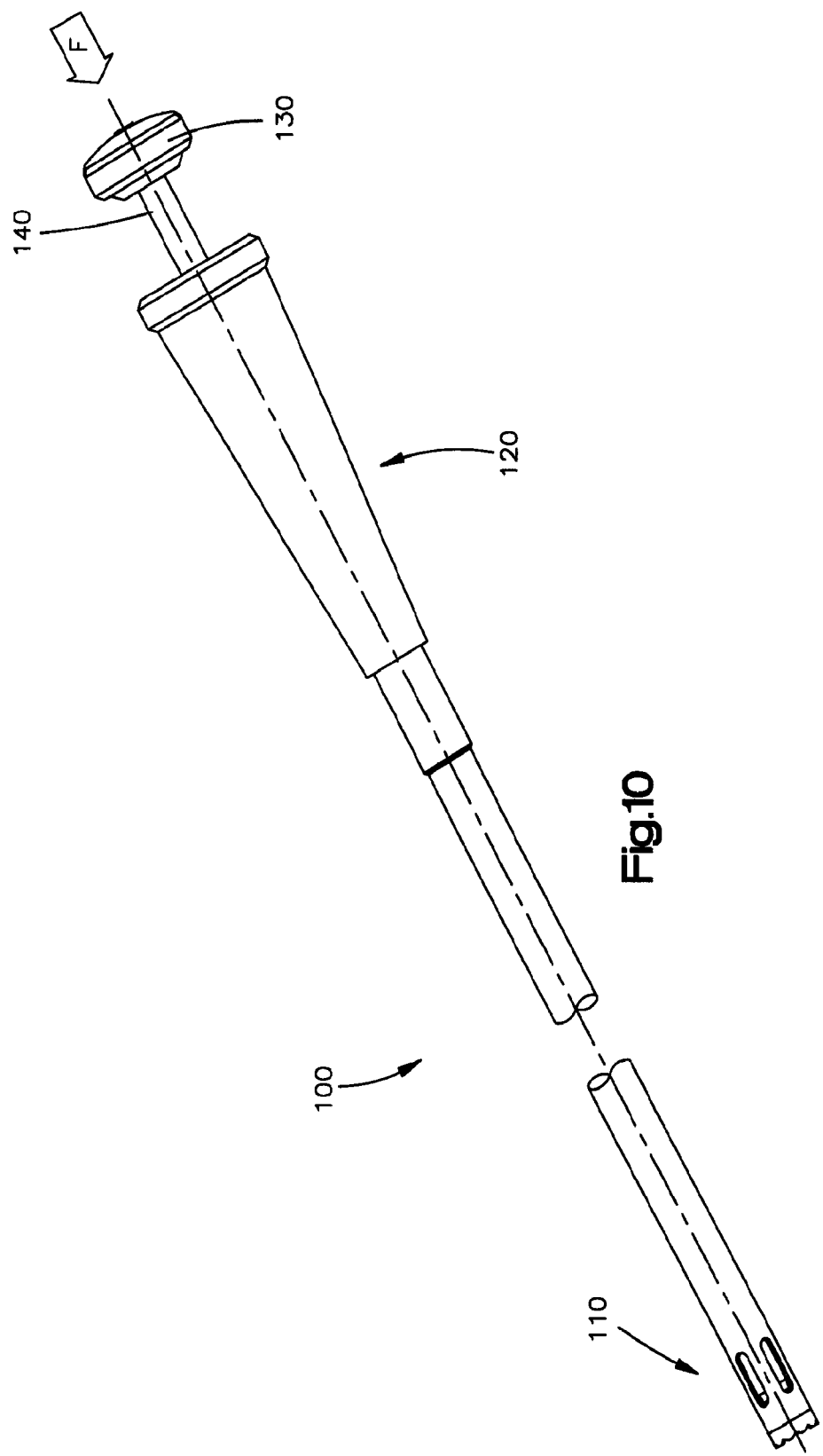
FIG. 10 illustrates a side perspective view of an insertion instrument according to a first preferred embodiment of the present invention.

Referring to FIG. 10, a first preferred embodiment of the insertion instrument 100 includes a distal tack engaging end 110, a handle 120, an impaction end 130 and an internal piston 140 for applying and/or transferring the impaction force F to the tack 50. The internal piston 140 may be integrally formed with the impaction end 130. Alternatively, the internal piston 140 may be operatively coupled to the impaction end 130. In use, the impaction force F preferably moves the internal piston 140 distally with respect to the handle 120 thereby driving the tack 50 into the patient's bone.

Figure 11:
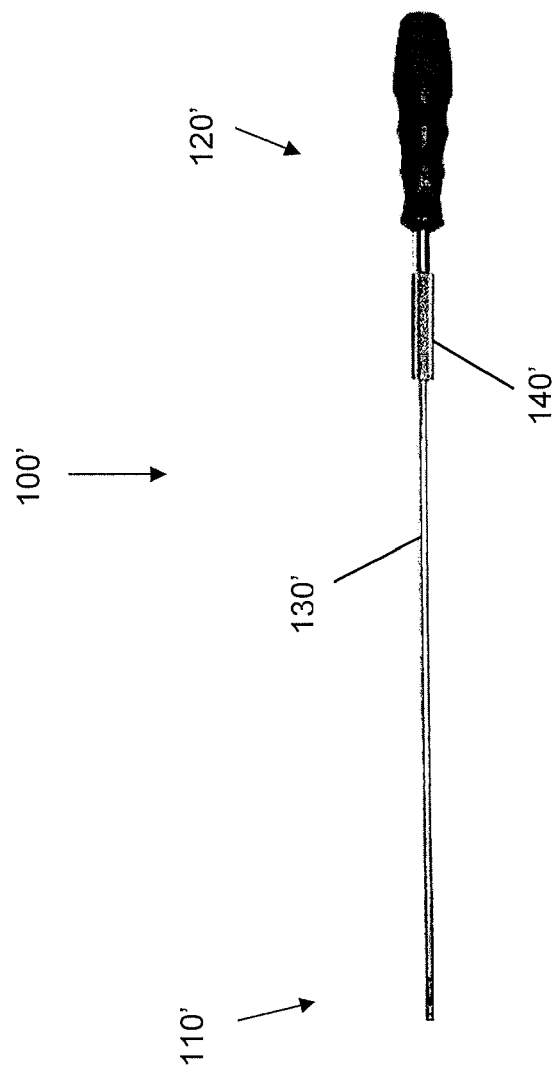
FIG. 11 illustrates a side perspective view of an insertion instrument according to a second preferred embodiment of the present invention.

Alternatively, referring to FIG. 11, a second preferred embodiment of the insertion instrument 100' includes a distal tack engaging end 110', a handle 120', an outer shaft 130' and an inner shaft or piston 140' for applying and/or transferring the impaction force F to the tack 50. In this second preferred embodiment, the impaction force F is preferably applied via a pushing action as a result of the inner shaft or internal piston 140' being slidably moveable relative to the outer shaft 130'. The inner shaft or piston 140' may be operatively associated or integrally formed with an outer member to facilitate gripping by the surgeon.

Referring to FIGS. 12A-13C, the insertion instrument 100 preferably also includes an automatic resetting mechanism 200 so that after the tack 50 has been driven into the patient's bone, the internal piston 140 automatically returns to its original position so that the surgeon may couple another tack 50 to the distal tack engaging end 110. The automatic resetting mechanism 200 preferably includes a unidirectional braking mechanism 210 and a position locking mechanism 250.

Referring to FIGS. 12A-12C, the braking mechanism 210 preferably includes a tapered or wedge-shaped inner surface 212 formed in the handle 120, one or more balls 220 circumferentially disposed about the internal piston 140 and a housing 230 operatively associated with the balls 220 and moveably located within the handle 120. In its initial position (as shown in FIGS. 12A and 12C), the braking mechanism 210 preferably also includes a spring force S via, for example, a spring, that biases the housing 230 proximally so that the balls 220 are biased into contact with the tapered or wedge-shaped inner surface 212 formed in the handle 120. Contact between the balls 220 and the tapered or wedge-shaped inner surface 212 formed in the handle 120 creates a braking force that generally prevents the internal piston 140 from moving proximally so that additional proximal advancement of the internal piston 140 (e.g., from left to right in FIGS. 12A-12C) causes the balls 220 to further contact the tapered or wedge-shaped inner surface 212 formed in the handle 120, which in turn creates an even greater braking force, which prevents the internal piston 140 from advancing any further in the proximal direction. In use, however, the internal piston 140 is free to move distally. As the internal piston 140 moves distally via the impaction force (e.g., from right to left in FIGS. 12A-12C), frictional forces between the internal piston 140 and the balls 220 causes the balls 220 to move distally and hence disengage and/or disassociate from the tapered or wedge-shaped inner surface 212 formed in the handle 120, thereby removing the braking force. The spring force S on the housing 230 preferably biases the balls 220 into contact the tapered or wedge-shaped inner surface 212 formed on the handle 120 so that as soon as the internal piston 140 ceases advancing distally, the housing 230 and balls 220 are immediately returned to their initial position and the braking force is immediately restored to hold or secure the position of the piston 140 in its sequentially advanced position.

Referring to FIGS. 13A-13C, the position locking mechanism 250 preferably includes a blocking mechanism 260, one or more balls 270 circumferentially disposed about the internal piston 140 and a housing 230 operatively associated with the balls 270 and moveably located within the handle 120. The housing 230 is preferably the same housing 230 used in the braking mechanism 210. Alternatively, the housing 230 may be separate and distinct or operatively coupled to the housing 230 used in the braking mechanism 210.

Referring to FIG. 13A, in its initial position, the balls 270 and housing 230 are preferably biased into a smaller diameter portion 280 formed in the handle 120 preferably via a spring force S. The spring force S preferably is the same spring force S that biases the housing 230 proximally so that the balls 220 are biased into contact with the tapered or wedge-shaped inner surface 212 in the braking mechanism 210. In its initial position, a second spring force $S_1$ acting from right to left in FIG. 13A preferably pushes the blocking mechanism 260 into constant contact with the balls 270. More preferably, the blocking mechanism 260 contacts the lower portion of the balls 270 such as, for example, the lower one-third of the balls 270 so that the blocking mechanism 260 creates a force vector on the balls 270 that acts in a radial direction (e.g., pushes the balls 270 radially outwards against the inner surface 282 of the smaller diameter portion 280 formed in the handle 120). Thus, in its initial position, the inner surface 282 of the smaller diameter portion 280 formed in the handle 120 prevents the balls 270 from being pushed radially outwards. Thereafter, distal movement of the internal piston 140 via the impaction force F (e.g., from right to left in FIGS. 13A-13C) causes the internal piston 140 to contact the housing 230 via, for example, a shoulder 232 formed on the internal piston 140, which in turn causes the housing 230 to move distally. Distal movement of the housing 230 enables the balls 270 via the spring force $S_1$ exerted by the blocking mechanism 260 to disassociate or leave the smaller diameter portion 280 formed in the handle 120 and to engage or move into a larger diameter portion 290 formed in the handle 120. That is, when the housing 230 moves distally, the constraint from the inner surface 282 of the smaller diameter portion 280 formed in the handle 120 is no longer present, which in turn enables the blocking mechanism 260 to push the balls 270 radially outwards into the larger diameter portion 290. Once located within the larger diameter portion 290, the balls 270 move into contact with the inner surface 292 of the larger diameter portion 290. The interface between the balls 270 and the inner surface 292 of the larger diameter portion 290 prevents the housing 230 from returning back to its initial position. Thus, the housing 230 is locked in this second position, as best shown in FIG. 13B. In addition, movement of the balls 270 into the larger diameter portion 290 enables the spring force $S_1$ to move the blocking mechanism 260 distally so that the blocking mechanism 260 is positioned beneath the balls 270 so that the balls 270 are located between the inner surface 292 of the larger diameter portion 290 and the blocking mechanism 260. Thus the balls 270 are prevented from returning to the smaller diameter portion 280.

The internal piston 140 is preferably biased via a spring force to return to its initial position (e.g., biased to move from left to right in FIGS. 13A-13C), a second shoulder 294 formed on the internal piston 140 contacts the blocking mechanism 260 causing the blocking mechanism 260 to move proximally back to its original position, which in turn removes the biasing force exerted by the blocking mechanism 260 on the balls 270. As a result, the balls 270 contact a resulting grooved edge 291 formed between the smaller diameter portion 280 and the larger diameter portion 290, which creates a force vector in the direction back toward the internal piston 140 causing the balls 270 to disassociate from the inner surface 292 of the larger diameter portion 290 and resulting in the balls 270 returning to the smaller diameter portion 280. Once the balls 270 are in the smaller diameter portion 280, the housing 230 is able to return to its initial position by the spring force S.

In use, the position locking mechanism 250 and the unidirectional braking mechanism 210 can be combined to create a ratcheting mechanism with an automatic resetting feature. In this configuration, the internal piston 140 is biased via a spring force S so that the piston 140 is forced proximally (e.g., left to right in FIGS. 12A-13C). When the piston 140 is moved from right to left or from the impaction end 130 toward the engaging end 110 via the impaction force F, the unidirectional braking mechanism 210 generally prevents the piston 140 from returning proximally, thereby enabling incremental movement of the piston 140 until the piston 140 has reached a predetermined depth. Subsequently, the shoulder 232 formed on the piston 140 contacts the housing 230, moving the housing 230 away from the tapered or wedge-shaped inner surface 212, thereby allowing the position locking mechanism 250 to engage. The unidirectional braking mechanism 210 is now disabled since the housing 230 is locked in this position. A spring force on the piston 140 causes the piston 140 to return to its initial position. As the piston 140 reaches its initial position, the second shoulder 294 formed on the piston 140 engages the blocking mechanism 260 and disengages the position locking mechanism 250. The housing 230 is now able to return to its initial position, which in turn causes the unidirectional locking mechanism 210 to re-engage.

Fixed Cartridge Driver

The tacks 50 can be loaded into the insertion instrument 100, 100' by inserting the tack 50 through a cannulated sleeve formed in the insertion instrument 100, 100'. Alternatively and/or in addition, the tack 50 may be operatively coupled to the distal tack engaging end 110, 110' of the insertion instrument 100, 100' by any means known including, but not limited to, via an o-ring. The o-ring functions as an interference fit that allows the head 54 of the tack 50 to pass upon impaction. A similar solution can be accomplished with properly toleranced polymer components.

Figure 14:
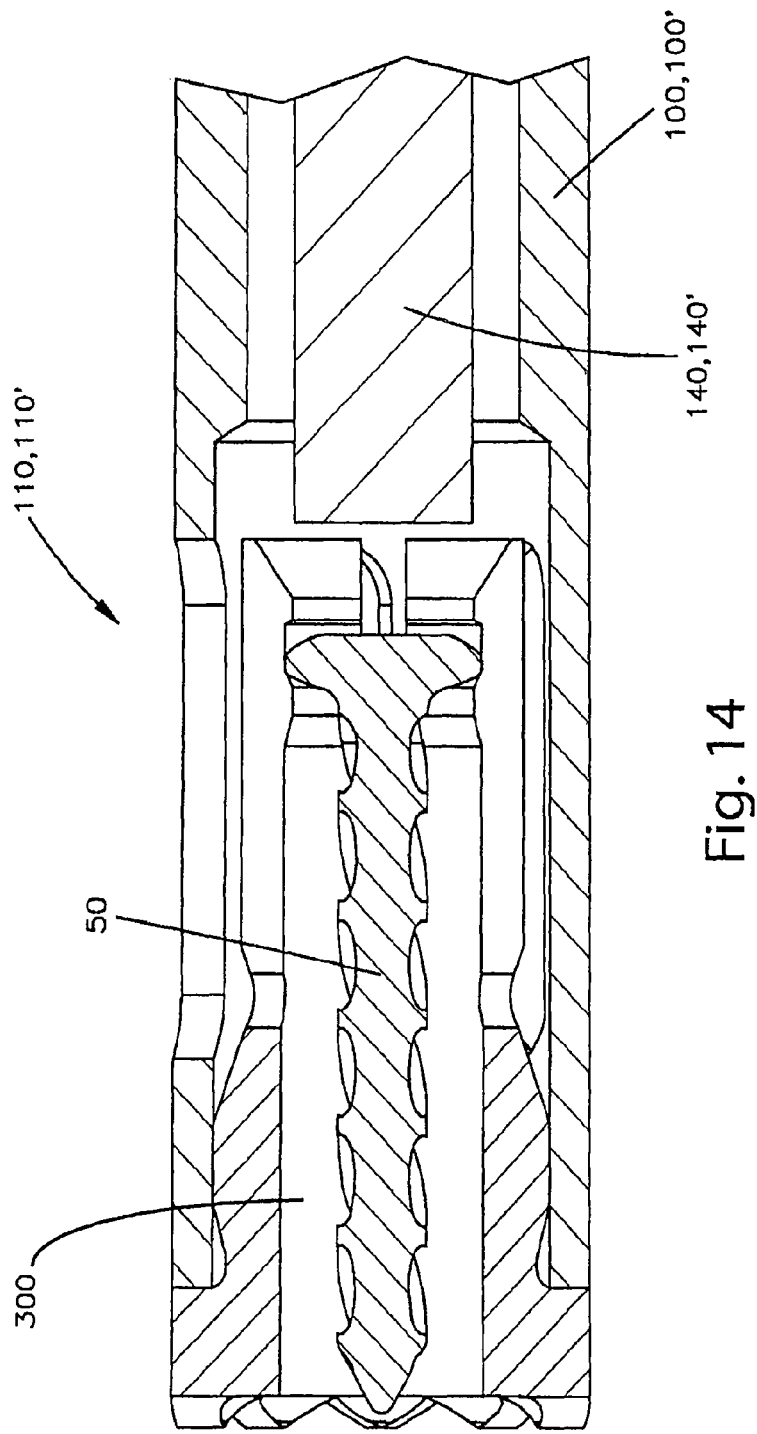
FIG. 14 is a cross-sectional view of a removable cartridge operatively coupled to a distal end of either of the insertion instruments of the first or second preferred embodiments in accordance with one aspect of the present invention.

Referring to FIG. 14, in a preferred embodiment, the tack 50 is contained in a tack containing cartridge 300, which is operatively coupled to the distal tack engaging end 110, 110' of the insertion instrument 100, 100'. That is, the tack 50 is preferably preloaded into the cartridge 300 and the cartridges 300 are coupled to the insertion instrument 100, 100' as needed. The cartridge 300 is preferably removably coupled to the insertion instrument 100, 100' by, for example, a snap fit connection, so that the cartridge 300 can be quickly removed and a new cartridge 300 can be attached, as necessary. Alternatively, the cartridge 300 may be coupled to the insertion instrument 100, 100' via, for example, a threaded connection, a clip-like mechanism, etc. Alternatively, the cartridge 300 may be configured to pick up a tack 50 by inserting the tack 50 through the distal end of the cartridge 300 and allowing it to engage a feature that holds the tack 50 in place.

The cartridge 300 preferably holds the tack 50 and aligns the main axis of the tack 50 with the internal piston 140, 140'. The cartridge 300 also preferably reinforces the tack 50 during impaction into vertebral bodies to prevent buckling of the tack 50 during implantation. The footprint of the cartridge 300 is preferably large enough to spread any additional impaction force F to minimize damage to the underlying bone, tissue, or prosthesis 10.

Roller Style Tack Driver

Figure 15B:
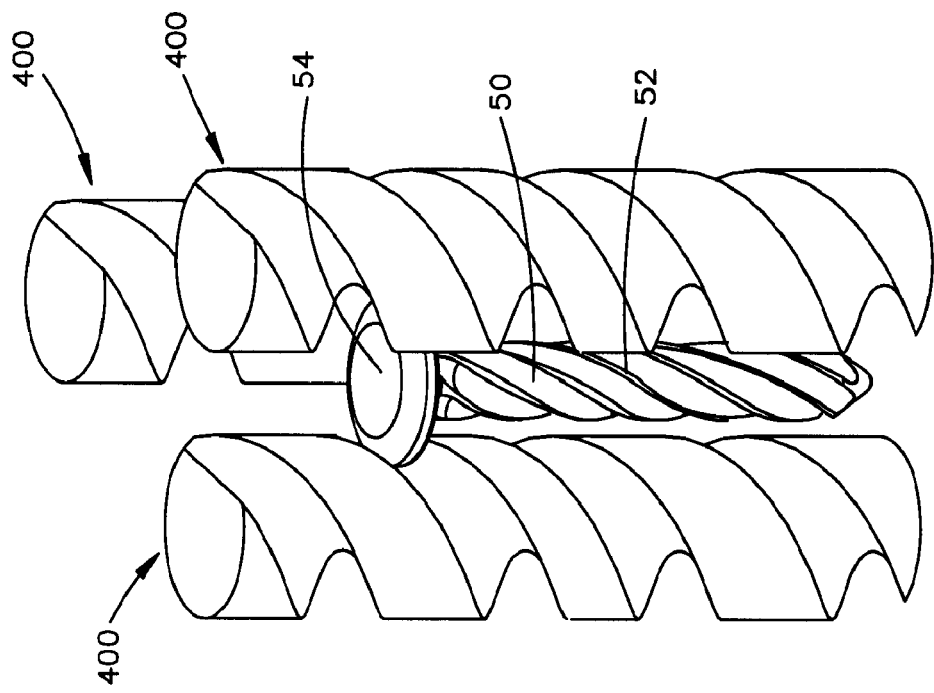
FIG. 15B is a top perspective view of the rollers and tack illustrated in FIG. 15A.
Figure 15A:
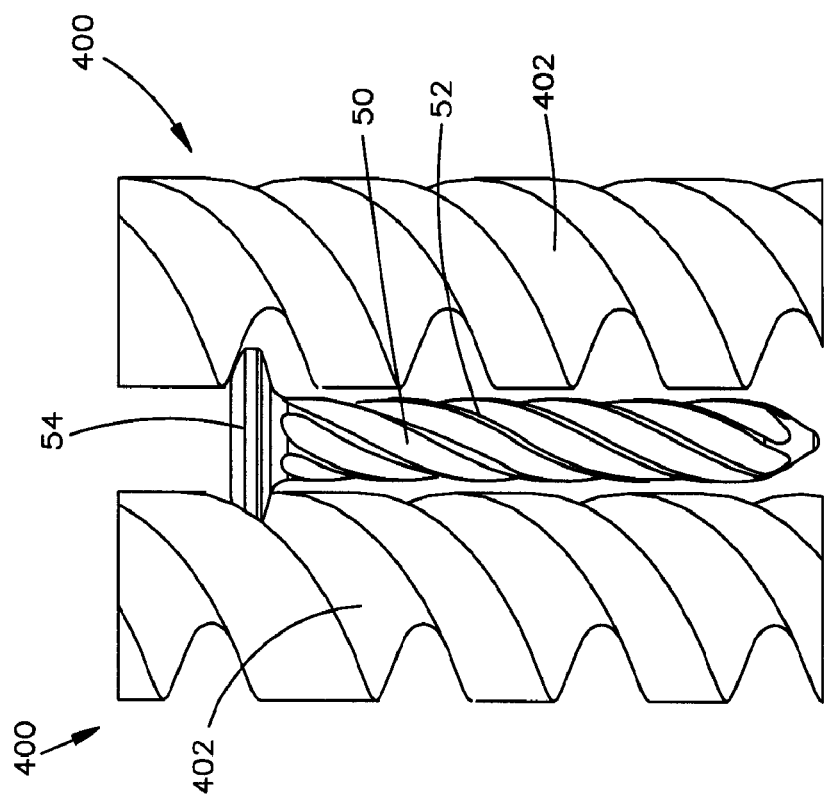
FIG. 15A is a side elevational view of a plurality of rollers for use in engaging any of the preferred tacks of the present invention during implantation in accordance with one aspect of the present invention.

Referring to FIGS. 15A and 15B, in situations where a tack 50 is impact driven down a cannulated insertion instrument, the inner diameter of the cannulated instrument preferably matches the outer diameter of the tack 50 as much as possible in order to minimize or prevent misalignment of the tack 50 inside of the cannulated shaft. Generally speaking, this misalignment is caused by the difference in diameters between the head portion 54 and the shaft portion 52 of the tack 50. The greater the size difference, the more misalignment that the tack 50 can encounter. This is because the inner diameter of the cannulated instrument must be large enough to receive the outer diameter of the head portion 54 of the tack 50 and permit the head portion 54 to move toward the distal end 110 of the instrument. This, however, enables the shaft portion 52 to move within the cannulated instrument thus increasing the likelihood of misalignment.

In use, the tack 50 is preferably constrained in an aligned position to ensure that the angle of insertion is maintained when driving the tack 50. One method for constraining the tack 50 during insertion is to incorporate a plurality of "rollers" 400 to provide axial constraints to the tack 50. Generally, the roller 400 is a cylindrical member having a helical cutout 402 along its axis for receiving at least a portion of the head portion 54 of the tack 50. Multiple rollers 400 are preferably circumferential disposed around the tack 50. Preferably, the rollers 400 are spaced diametrically around the tack 50 at equal intervals. For example, three rollers 400 may be used, wherein the rollers 400 are preferably spaced at one hundred twenty degrees) (120°) relative to each other.

The outer diameter of the rollers 400 are preferably tangent to the shaft 52 of the tack 50 to ensure that the shaft portion 52 of the tack 50 is always aligned with the rollers 400. The helical cut 402 along the roller 400 has a minor diameter that closely matches the diameter of the head portion 54 of the tack 50 so that the helical cutout 402 constrains the head portion 54 of the tack 50. The helical cut 402 along the roller 400 preferably has a high pitch so that in use, as the tack 50 is impacted, the head portion 54 is able to engage the helical cutouts 402, which in turn causes the rollers 400 to spin within the cannulated shaft. This allows the tack 50 to advance forward and still remain fully constrained along the entire length thereof. Since the tack 50 must be impacted to spin the rollers 400 and advance the tack 50, it provides additional stability since it prevents a tack 50 from unintentional falling out of the cannulated instrument. If no force is acting on the tack 50, it will typically not advance through the mechanism. Alternatively, the helical cut 402 may include a low pitch such that in use, as the tack 50 is impacted, the tack 50 will not move proximally and/or distally. Rather, a driving mechanism such as, for example, a motor or manual mechanism, could be attached to the rollers 400 to spin them. Rotating the rollers 400 in turn drives the tack 50 distally and/or proximally. This version is particularly advantageous where a surgeon prefers a power tool or desires additional precision control over insertion speed and depth.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

The invention claimed is:

1. A method, comprising
driving a tack through a low load bearing prosthesis positioned against the spine of a patient and into the spine with an insertion instrument comprising a distal tack engaging end, an internal piston, a cannulated shaft, and a tack surrounded by a plurality of rollers, each of the rollers comprising a cylindrical member having a helical cutout for receiving at least a portion of a head portion of the tack, by applying an impaction force to the insertion instrument so the piston moves distally into contact with the tack to drive the tack through the prosthesis and into the spine; and repeating the method as necessary.

2. The method of claim 1, wherein the tack includes an external flange extending from an outer surface of the tack so that the tack rotates as the tack is being impact driven into the spine.

3. The method of claim 1, wherein the tack includes one or more barbs that can be impact-driven into the spine in one direction and resist motion in the opposite direction.

4. The method of claim 1, wherein the tack is contained in a cartridge operatively coupled to the distal tack engaging end of the insertion instrument.

5. The method of claim 1, wherein the tack is inserted into the cannulated shaft.

6. The method of claim 1, wherein the insertion instrument includes a resetting mechanism so that upon release of the impaction force, the internal piston automatically returns to its original position.

7. The method of claim 6, wherein the resetting mechanism includes a unidirectional braking mechanism and a position locking mechanism.

8. The method of claim 1, wherein applying the impaction comprises striking the proximal end of the insertion instrument with a hammer or mallet.

9. An insertion instrument, comprising a distal tack engaging end, an internal piston, a cannulated shaft, and a plurality of rollers, each of the rollers comprising a cylindrical member having a helical cutout for receiving at least a portion of a head portion of a tack.

10. The insertion instrument of claim 9, further comprising a tack.

11. The insertion instrument of claim 10, wherein the tack is contained in a cartridge.

12. The insertion instrument of claim 11, wherein the cartridge is operatively coupled to the distal tack engaging end.

13. The insertion instrument of claim 10, wherein the tack includes an external flange extending from an outer surface.

14. The insertion instrument of claim 10, wherein the tack includes one or more barbs that can be impact driven into the spine in one direction and resist motion in the opposite direction.

15. The insertion instrument of claim 9, further comprising a resetting mechanism for automatically returning the piston to its original position after the piston is moved distally.

16. The insertion instrument of claim 15, wherein the resetting mechanism includes a unidirectional braking mechanism and a position locking mechanism.

* * * * *